United States Patent
Oroskar et al.

(10) Patent No.: US 12,195,438 B2
(45) Date of Patent: *Jan. 14, 2025

(54) PROCESS FOR REMOVING THC FROM CANNABINOIDS

(71) Applicant: Kazmira LLC, Watkins, CO (US)

(72) Inventors: Anil Rajaram Oroskar, Oak Brook, IL (US); Kunal Gulati, Naperville, IL (US); David House, Arlington Heights, IL (US); Gautham Oroskar, Oak Brook, IL (US); Feng Peng, Chicago, IL (US); Michelle Chen, Naperville, IL (US); Faridedin Adel, Arlington Heights, IL (US); Pulak Sharma, Aurora, CO (US); Justin Fulford, Watkins, CO (US)

(73) Assignee: KAZMIRA LLC., Watkins, CO (US)

( * ) Notice: Subject to any disclaimer, the term of this patent is extended or adjusted under 35 U.S.C. 154(b) by 28 days.

This patent is subject to a terminal disclaimer.

(21) Appl. No.: 17/548,249

(22) Filed: Dec. 10, 2021

(65) Prior Publication Data

US 2022/0185787 A1      Jun. 16, 2022

Related U.S. Application Data

(60) Provisional application No. 63/123,933, filed on Dec. 10, 2020.

(51) Int. Cl.
    *C07D 311/78*   (2006.01)
    *B01D 15/18*    (2006.01)
    *C07C 37/82*    (2006.01)
    *C07C 37/84*    (2006.01)

(52) U.S. Cl.
    CPC .................. *C07D 311/78* (2013.01)

(58) Field of Classification Search
    CPC ....... C07C 37/685; C07C 37/82; C07C 37/84; B01D 15/1821
    See application file for complete search history.

(56) References Cited

U.S. PATENT DOCUMENTS

| | | |
|---|---|---|
| 2,985,589 A | 5/1861 | Broughton |
| 2,304,669 A | 12/1942 | Roger |
| 8,343,553 B2 | 1/2013 | Hospodor |
| 9,034,395 B2 | 5/2015 | Whittle |
| 9,044,390 B1 | 6/2015 | Speier |
| 9,199,960 B2 | 12/2015 | Ferri |
| 9,358,259 B2 | 6/2016 | Hospodor et al. |
| 10,189,762 B1 | 1/2019 | Oroskar et al. |
| 10,413,845 B1 | 9/2019 | Tegen et al. |
| 10,414,709 B1 | 9/2019 | Tegen et al. |
| 10,604,464 B2 | 3/2020 | Oroskar et al. |
| 10,799,546 B1 | 10/2020 | Jansen et al. |
| 10,843,991 B2 | 11/2020 | Oroskar et al. |
| 11,078,145 B2 | 8/2021 | Oroskar et al. |
| 2004/0033280 A1 | 2/2004 | Whittle |
| 2005/0266108 A1 | 12/2005 | Flockhart et al. |
| 2006/0167283 A1 | 7/2006 | Flockhart et al. |
| 2008/0167483 A1 | 7/2008 | Whittle et al. |
| 2012/0294887 A1 | 11/2012 | Saunois et al. |
| 2015/0126596 A1 | 5/2015 | Gutman et al. |
| 2018/0200315 A1 | 7/2018 | Silver |
| 2018/0206518 A1 | 7/2018 | Silver |
| 2018/0333446 A1 | 11/2018 | Shan et al. |
| 2018/0362429 A1 | 12/2018 | Zhang et al. |
| 2019/0010106 A1 | 1/2019 | Oroskar et al. |
| 2019/0010110 A1 | 1/2019 | Oroskar et al. |
| 2019/0144414 A1 | 5/2019 | Erfurt et al. |
| 2019/0210946 A1 | 7/2019 | Qu et al. |
| 2019/0276420 A1 | 9/2019 | Tegen et al. |
| 2020/0255389 A1 | 8/2020 | Tegen et al. |
| 2020/0399194 A1 | 12/2020 | Oroskar et al. |
| 2021/0363083 A1 | 11/2021 | Oroskar et al. |

FOREIGN PATENT DOCUMENTS

| | | |
|---|---|---|
| CN | 110724589 A | 1/2020 |
| EP | 1536810 B1 | 8/2012 |
| WO | WO 2003/074144 A2 | 9/2003 |
| WO | WO 2004/026802 A1 | 4/2004 |
| WO | WO 2016/187679 A1 | 12/2016 |
| WO | WO 2017/026897 A1 | 2/2017 |
| WO | WO 2017/194173 A1 | 11/2017 |

(Continued)

OTHER PUBLICATIONS

U.S. Appl. No. 15/644,112, filed Jul. 7, 2017.
U.S. Appl. No. 16/113,947, filed Aug. 27, 2018.
U.S. Appl. No. 17/011,780, filed Sep. 3, 2020.
U.S. Appl. No. 17/392,718, filed Aug. 3, 2021.
U.S. Appl. No. 17/830,098, filed Jun. 1, 2022.
Elixinol LLC, "Pros and Cons of Hemp Oil Extraction Techniques," https://elixinolcbd.com/blogs/buyers-guide/16641671-pros-and-cons-of-hemp-oil-extraction-techniques (Mar. 12, 2015).

(Continued)

*Primary Examiner* — Sikarl A Witherspoon
(74) *Attorney, Agent, or Firm* — Leydig, Voit & Mayer, Ltd.

(57) ABSTRACT

A method of removing THC and/or THCA from a mixture is provided, the mixture including at least one other cannabinoid. The method comprises passing a first feedstock stream through a first chromatographic resin arranged in a simulated moving bed (SMB) chromatography configuration to provide a primary raffinate stream, preparing a second feedstock stream, the second feedstock stream comprising the primary raffinate stream or a concentrated primary raffinate stream, and passing the second feedstock stream through a second chromatographic resin to provide an eluate stream, the eluate stream having less than 0.3 wt % THC on a solvent free basis. The cannabinoid products can be used in various pharmaceutical and nutraceutical applications.

30 Claims, 13 Drawing Sheets

(56) References Cited

FOREIGN PATENT DOCUMENTS

| WO | WO 2019/010419 A1 | 1/2019 |
| WO | WO 2019/173582 A1 | 9/2019 |
| WO | WO 2020/028198 A1 | 2/2020 |
| WO | WO 2020/046822 A1 | 3/2020 |
| WO | WO 2020/117688 A2 | 6/2020 |

OTHER PUBLICATIONS

Konen, "Why Ethanol Works So Well for Cannabis Extraction," Capna Labs, https://www.leafly.com/news/industry/ethanol-cannabis-extraction (Aug. 31, 2016).

Meyer et al., "Development of a rapid method for the sequential extraction and subsequent quantification of fatty acids and sugars from avocado mesocarp tissue," *J. Agric. Food Chem.*, 56(16): 7439-7445 (2008).

Shimadzu Corporation, HPLC-015 Application News—"Potency Testing in Cannabis Extracts Using a High Resolution Method with Cannabis Analyzer for Potency," (Feb. 2017).

Shimadzu Corporation, HPLC-016 Application News—"Potency Testing in Cannabis Extracts Using a High Sensitivity Method with Cannabis Analyzer for Potency," (Feb. 2017).

Shimadzu Corporation, HPLC-017 Application News—"Potency Testing in Cannabis Extracts Using a High Throughput Method with Cannabis Analyzer for Potency," (Feb. 2017).

European Patent Office, International Search Report and Written Opinion of the International Searching Authority in International Application No. PCT/US2018/041096 (Oct. 31, 2018).

European Patent Office, International Search Report and Written Opinion of the International Searching Authority in International Application No. PCT/US2019/048160 (Jan. 24, 2020).

European Patent Office, International Search Report and Written Opinion of the International Searching Authority in International Application No. PCT/US2021/062920 (Apr. 4, 2022).

PROCESS FOR REMOVING THC FROM CANNABINOIDS

CROSS-REFERENCE TO RELATED APPLICATIONS

This patent application claims the benefit of U.S. Provisional Application No. 63/123,933, filed Dec. 10, 2020, and entitled, "Process for Removing THC from Cannabinoids," which is incorporated in its entirety herein by this reference.

BACKGROUND

The legalization of medicinal *Cannabis* is occurring across the United States and in many other countries. As a result, the global demand for cannabinoids is increasing. In addition, a number of recent medical studies report health benefits of many cannabinoids. *Cannabis* contains over 85 cannabinoids, most of them have been found to have therapeutically beneficial properties. The most widely known cannabinoids found in cannabis known to have the most therapeutic properties are cannabidiol (CBD) and tetrahydrocannabinol (THC). A number of other cannabinoids, such as cannabichromene (CBC), cannabigerol (CBG), and cannabinol (CBN), also have been shown to exhibit health benefits.

Cannabinoids are generally known as being psychoactive; however, the psychoactive properties of cannabinoid products depend on the amount of tetrahydrocannabinol (THC) in the products. Accordingly, there is demand for cannabinoid products that are essentially free of tetrahydrocannabinol (THC), or do not contain tetrahydrocannabinol (THC).

Recently, a number of medical applications for cannabidiol (CBD) relate to treatment of conditions that effect children. Because physicians and parents do not want their children consuming a psychoactive product, there is growing demand for cannabidiol (CBD) without tetrahydrocannabinol (THC). Associated with this demand for a tetrahydrocannabinol (THC) free product, there is a demand for botanically derived and extracted products, rather than synthetically derived products.

The terms hemp and cannabis refer to the genus *Cannabis*, which contains three species *Cannabis sativa*, *Cannabis indica*, and *Cannabis ruderalis*. All three species are of the family Cannabaceae, which also includes the genus *Humulus*, or hops. *Cannabis* is a flowering plant that is indigenous to central Asia and India. Humans have been cultivating and using cannabis for thousands of years, going back to the ancient Romans, Greeks, and the Islamic empires of the Middle East and Africa.

There are at least 113 different cannabinoids present in the cannabis plant. All of the classes of cannabinoids are derived from a common precursor compound, cannabigerol (CBG). The cannabis plant also contains a variety of terpenoids. Most such compounds are lipophilic and phenolic.

Below are the structures of many common cannabinoids:

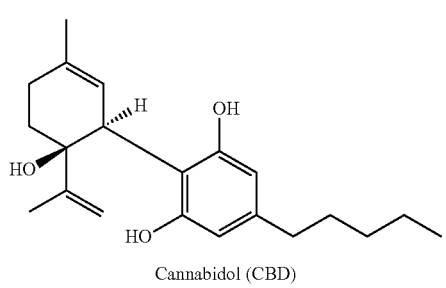

Cannabidol (CBD)

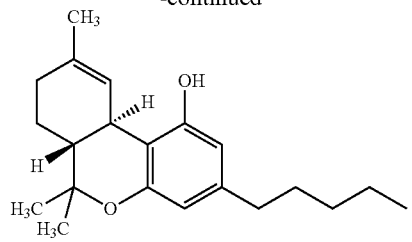

Tetrahydrocannabinol (THC)

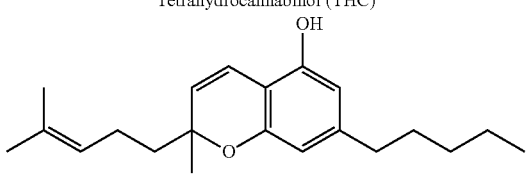

Cannabichromene (CBC)

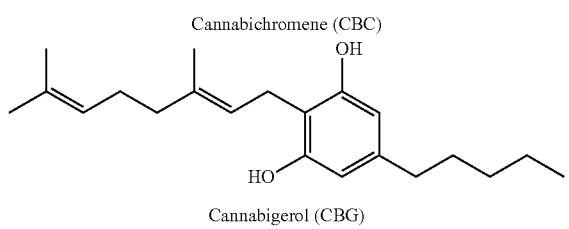

Cannabigerol (CBG)

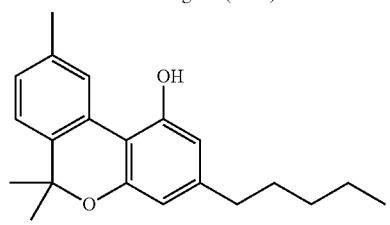

Cannabinol (CBN)

Cannabinoids can be extracted from dried hemp and cannabis leaves of the three species *Cannabis sativa*, *Cannabis indica*, and *Cannabis ruderalis* using a hydrocarbon solvent such as butane, a supercritical solvent such as carbon dioxide, or ethanol. Butane extraction and supercritical $CO_2$ extraction, have accounted for the majority of production of cannabinoid concentrates currently available on the market. A third extraction method, based on ethanol has been gaining market share as a solvent of choice for manufacturing high-quality cannabis extracts.

U.S. Patent Application Publication No. 2019/0010110 A1, which is hereby incorporated by reference, discloses methods to isolate and purify cannabinoids using column chromatography. More particularly, U.S. Patent Application Publication No. 2019/0010110 A1 discloses methods of purifying cannabinoids using Simulated Moving Bed (SMB) technology.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

While methods of purifying cannabinoids by Simulated Moving Bed (SMB) chromatography are known, there remains a need for improved methods for purifying cannabinoid products. For example, there is a continued need for techniques which provide cannabinoid products with enhanced purity (e.g., acceptable levels of THC).

It will be appreciated that this background description has been created by the inventors to aid the reader, and is not to be taken as an indication that any of the indicated problems were themselves appreciated in the art. While the described principles can, in some aspects and embodiments, alleviate the problems inherent in other systems and techniques, it will be appreciated that the scope of the protected innovation is defined by the attached claims, and not by the ability of any disclosed feature to solve any specific problem noted herein.

SUMMARY

Embodiments of the present disclosure are directed to methods for the purification of cannabinoids and the removal of THC/THCA from dried hemp and cannabis leaves. For example, the methods of the disclosure can be used to separate a desired cannabinoid (e.g., cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof), i.e., to increase its purity, from other cannabinoids, such as tetrahydrocannabinol.

Thus, in some aspects, a method of removing THC and/or THCA from a mixture, the mixture including THC and/or THCA and at least one cannabinoid is provided. The method includes preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, the primary raffinate stream having less than 0.9 wt % THC (e.g., less than 0.8 wt % THC, less than 0.75 wt % THC, or less than 0.5 wt % THC) on a solvent free basis and optionally a higher weight percentage of at least one cannabinoid than in the first feedstock stream on a solvent free basis; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent and the second feedstock stream having less than 0.9 wt % THC (e.g., less than 0.8 wt % THC, less than 0.75 wt % THC, or less than 0.5 wt % THC) on a solvent free basis; and passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

In some aspects, a method of removing THC and/or THCA from a mixture, the mixture including THC and/or THCA and at least one cannabinoid is provided. The method includes preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, wherein passing the first feedstock stream through the first chromatographic resin arranged in a simulated moving bed (SMB) chromatography configuration removes greater than 50 wt % (e.g., greater than 60 wt %, greater than 70 wt %, greater than 80 wt %, or greater than 90 wt %) of the THC from the mixture as measured by the mass of THC in the primary raffinate compared to the mass of THC in the mixture; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent; and passing the second feedstock stream through a second chromatographic resin to provide an eluate stream, wherein passing the second feedstock stream through the second chromatographic resin removes up to 50 wt % (e.g., up to 40 wt %, up to 30 wt %, up to 20 wt %, or up to 10 wt %) of the THC from the mixture as measured by the mass of THC in the eluate stream compared to the mass of THC in the mixture.

In some aspects, a method of removing THC and/or THCA from a mixture, the mixture including THC and/or THCA and at least one cannabinoid is provided. The method includes preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, the SMB extract stream having a higher weight percentage of THC and/or THCA on a solvent free basis and optionally a higher weight percentage of at least one cannabinoid than in the first feedstock stream on a solvent free basis; optionally removing at least a portion of the first solvent from the SMB extract stream to produce a concentrated SMB extract stream; preparing a second feedstock stream, the second feedstock stream comprising the SMB extract stream or the concentrated SMB extract stream and a second solvent; and passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

A cannabinoid product (e.g., cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof) having less than 0.3 wt % (e.g., less than 0.2 wt %, less than 0.1 wt %, less than 0.5 wt %, trace, or undetectable) THC on a solvent free basis is also provided. The cannabinoid product can be used in various pharmaceutical and nutraceutical applications.

BRIEF DESCRIPTION OF THE DRAWINGS

The accompanying drawings are included to provide a further understanding of the disclosure. The drawings illustrate embodiments of the disclosure and together with the description serve to explain the principles of the embodiments of the disclosure.

DETAILED DESCRIPTION OF EXEMPLARY EMBODIMENTS

Figure 1:
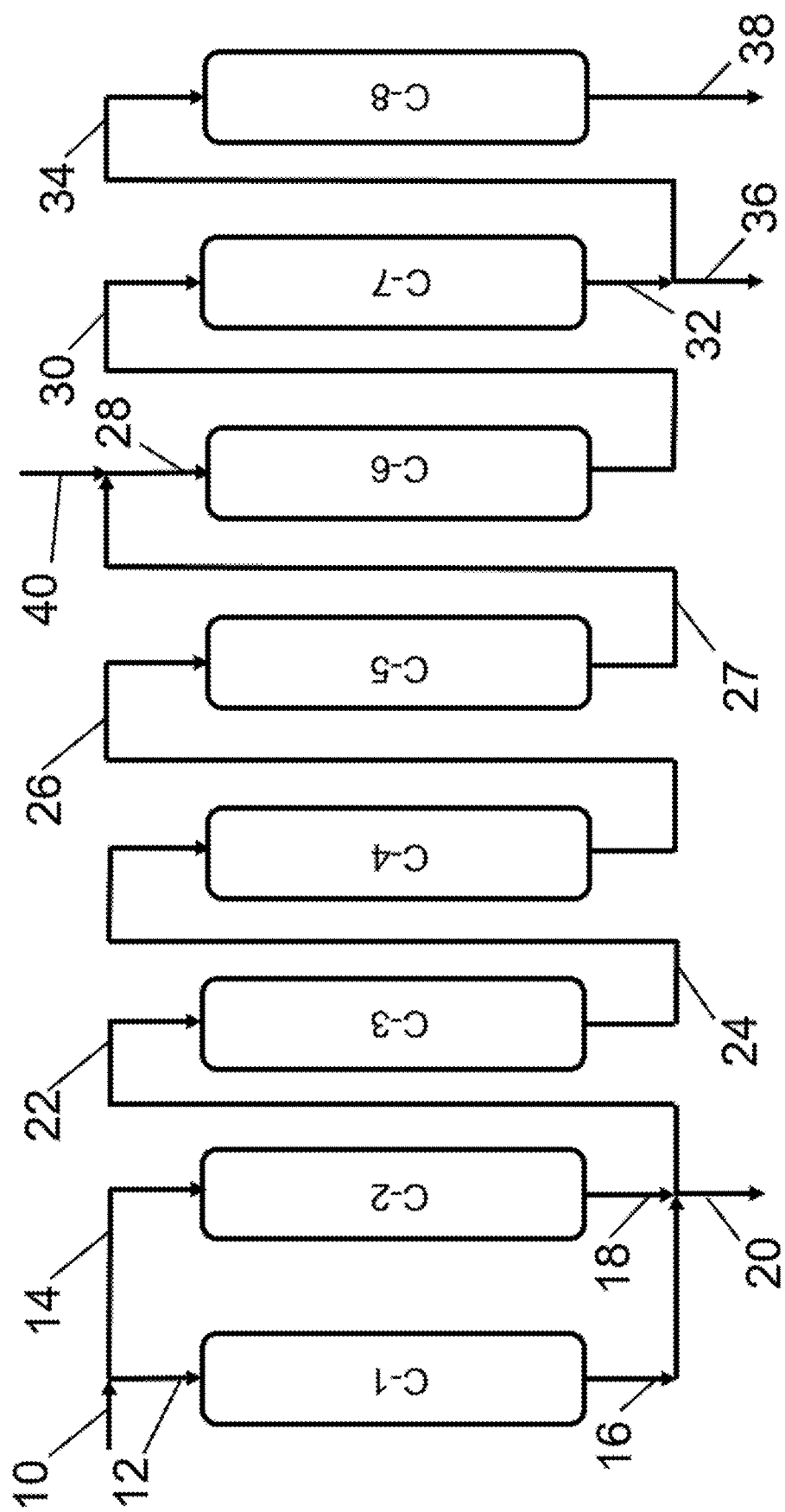
FIG. 1 is a schematic process flow diagram illustrating a configuration of the simulated moving bed cycle for a simulated moving bed (SMB) configuration in one embodiment of the disclosure.

Industrial hemp, or agricultural hemp, and medical marijuana both come from the *Cannabis Sativa* L. plant. Industrial hemp, which is often referred to as "hemp stalk," grows differently than THC-containing cannabis, and looks similar to bamboo. Cannabinoids are a family of naturally occurring $C_{21}$ terpenophenolic compounds uniquely produced in cannabis. Marijuana usually refers to a mixture of leaves and flowering heads of the pistillate plant of *Cannabis sativa* from which tetrahydrocannabinols (THCs) are isolated. THCs contain two main isomeric forms, depending on the position of the double bond. The position of the double bond and the stereochemistry of these THCs have been confirmed by nuclear magnetic resonance and X-ray structure.

Extracting active ingredients from cannabis routinely extracts a number of impurities which are difficult to remove from the finished product; and, therefore a large number of purification steps, including expensive column chromatography, are required in conventional methods to isolate components.

The following are typical abbreviations for commonly found cannabinoids in the extract of hemp leaves:

| | |
|---|---|
| THC | Tetrahydrocannabinol |
| THCV | Tetrahydrocannabivarin |
| CBG | Cannabigerol |
| CBGA | Cannabigerolic acid |
| CBC | Cannabichromene |
| CBCA | Cannabichromenic acid |
| CBD | Cannabidiol |
| CBN | Cannabinol |
| THCA | Tetrahydrocannabinolic Acid |
| CBDA | Cannabidiolic Acid |
| CBDV | Cannabidivarin |

In various embodiments, the present disclosure provides methods of removing THC and/or THCA from a mixture, the mixture including THC and/or THCA and at least one cannabinoid. Generally, the mixture is obtained from extracting and/or isolating cannabinoids from plants of the genus *Cannabis*, which contains three species, namely *Cannabis sativa*, *Cannabis indica*, and *Cannabis ruderalis*. The methods of the disclosure utilize column chromatography for removing THC and/or THCA and isolating the cannabinoid. Any suitable cannabinoid can be purified and isolated. For example, the cannabinoid can be cannabidiol (CBD), cannabidiolic acid (CBDA), cannabichromene (CBC), cannabinol (CBN), cannabigerol (CBG), cannabigerolic acid (CBGA), cannabidivarin (CBDV), or a mixture thereof. The resulting extracted cannabinoid can be purified to high levels, thereby allowing for their use in various pharmaceutical and nutraceutical applications. For example, in certain aspects purified CBD or CBC can be obtained, which has the benefits of CBD or CBC without the alternative effects of psychoactive THC.

Generally, the method of removing THC and/or THCA from a mixture, the mixture including THC and/or THCA and at least one cannabinoid includes using at least two chromatographic steps (e.g., column chromatography). Any suitable adsorbent (e.g., OR-1, OR-2, OR-2 prime, OR-3, OR-4, OR-5, OR-5 prime, OR-11, or a combination thereof) can be used for the chromatographic methods described herein. The adsorbent can be utilized in any suitable arrangement (e.g., single column chromatography, batch column chromatography, SMB chromatography, or a combination thereof). Typically, the method comprises using more than one adsorbent and more than one arrangement to achieve the desired purity of the cannabinoid.

The methods of the disclosure can be used to purify a cannabinoid by removing THC and/or THCA from a mixture, the mixture including THC and/or THCA and at least one cannabinoid. As used herein, the terms "purify" and "purification" can refer to a process of separating at least one cannabinoid from THC and/or THCA so as to provide a composition wherein at least one cannabinoid is present in the composition in a higher concentration on a solvent free basis. Embodiments of a method following principles of the present disclosure can be used to separate a cannabinoid and at least one impurity to produce a higher purity of the cannabinoid.

In some embodiments, a method following principles of the present disclosure can be used to remove additional impurities other than THC and/or THCA. The additional impurities can be considered any compound or mixture of compounds that are not the desired target cannabinoid. For example, the additional impurities can include one or more of waxes, lipids, pigments, or mixtures thereof. In some embodiments, the additional impurities can include other cannabinoids, e.g., a second cannabinoid, a third cannabinoid, etc., that are not the desired target cannabinoid.

The purity of a cannabinoid can be measured by any suitable means known to a person of ordinary skill in the art. In some embodiments, the purity of a cannabinoid is measured using high performance liquid chromatography (HPLC). In some embodiments, the purity of a cannabinoid is measured using weight percentage of the solid/oil content. As used herein, the phrases "solid content," "oil content," and "solid/oil content" can be used interchangeably to refer to the amount of a compound in a mixture on a solvent free basis. A skilled artisan will recognize that any constituent described herein can exist as a solid or an oil depending on the other constituents in the solvent free mixture. In other words, as used herein, the phrase "as measured by weight percentage of the solid/oil content" refers to the amount of a compound in a mixture on a solvent free basis. If the weight percentage of a constituent in the solid/oil content increases, the constituent is considered to be more pure. If the weight percentage of a constituent in the solid/oil content decreases, the constituent is considered to be less pure. To illustrate, a constituent having a weight percentage of 15% is more pure than if it had a weight percentage of 10%. Similarly, a constituent having a weight percentage of 90% is more pure than if it had a weight percentage of 75%.

As used herein, the term "solid/oil concentration" refers to the mass of solids/oils per volume of liquid in a given stream and is expressed as grams/Liter. The mass of the solids/oils content in a stream is determined by subjecting a fixed volume of the sample, typically 1 ml, to an effective amount of heat, up to 80° C., at atmospheric pressure for a time sufficient to fully evaporate the sample to dryness, typically 1-2 hours.

Embodiments of a method following principles of the present disclosure can use normal-phase chromatography and/or reversed-phase chromatography. In some embodiments, the methods of the disclosure employ a process known as reversed-phase chromatography. As used herein, the term "reversed-phase chromatography" employs a polar (aqueous) mobile phase. As a result, hydrophobic molecules in the polar mobile phase tend to adsorb to the hydrophobic stationary phase, and hydrophilic molecules in the mobile phase will pass through the column and are eluted first. Accordingly, any suitably stationary phase adsorbent (i.e., chromatographic resin) can be used in methods of the disclosure.

The stationary phase adsorbents may be disposed in a single adsorbent bed or may be disposed in a single column or series of single columns containing multiple adsorbent bed zones. Embodiments of the present disclosure employ separate stationary phase adsorbents in carrying out the overall process of the disclosure. A list of exemplary stationary phases (i.e., chromatographic resins) for use in various embodiments of the methods of the disclosure are as follows.

OR-1 is a modified activated carbon adsorbent which was heat treated to provide a highly hydrophobic adsorbent which is essentially free of hydroxyl groups. In some embodiments, OR-1 has an average particle size range of from about 40 microns to about 1700 microns (e.g., about 50 microns to about 1000 microns, about 50 microns to about 500 microns, about 100 microns to about 500 microns, about 40 microns to about 180 microns, about 70 microns to about 300 microns, about 100 microns to about 250 microns, or 177 microns and 250 microns). In some embodiments, OR-1 has an iodine number (a measure of the micropore content of the activated carbon) greater than about 900 mg/g (e.g., greater than about 1000 mg/g, greater than about 1250 mg/g, greater than about 1500 mg/g, or greater than about 2000 mg/g).

OR-2 is a modified hydrophobic adsorbent comprising a styrene-divinylbenzene (DVB) resin or a poly(methyl methacrylate) (PMMA) resin. In some embodiments, the styrene-divinylbenzene (DVB) resin has from about 4% to about 8% (e.g., about 4%, about 4.5%, about 5%, about 5.5%, about 6%, about 6.5%, about 7%, about 7.5%, or about 8%) crosslinking. In some embodiments, OR-2 has an average particle size range of from about 25 microns to about 300 microns (e.g., about 25 microns to about 200 microns, about 25 microns to about 100 microns, about 100 microns to about 300 microns, about 200 microns to about 300 microns, or about 50 microns to about 250 microns). In some embodiments, OR-2 has an average bulk density of from about 0.4 g/mL to about 0.6 g/mL (e.g., about 0.4 g/mL, about 0.45 g/mL, about 0.5 g/mL, about 0.55 g/mL, or about 0.6 g/mL), an average surface area of from about 450 $m^2/g$ to about 550 $m^2/g$ (e.g., about 450 $m^2/g$ to about 525 $m^2/g$, about 450 $m^2/g$ to about 500 $m^2/g$, about 475 $m^2/g$ to about 550 $m^2/g$, or about 500 $m^2/g$ to about 550 $m^2/g$). In some embodiments, OR-2 has an average pore volume of from about 0.7 mL/g to about 0.9 mL/g (e.g., about 0.7 g/mL, about 0.75 g/mL, about 0.8 g/mL, about 0.85 g/mL, or about 0.9 g/mL). In certain embodiments of OR-2 resin, the modified hydrophobic adsorbent (i.e., hydrophobic resin) is a C18 resin.

OR-2 prime (i.e., OR-2') is a hydrophobic resin. In some embodiments, OR-2 prime has an average particle diameter of from about 25 microns to about 300 microns (e.g., about 25 microns to about 200 microns, about 25 microns to about 100 microns, about 100 microns to about 300 microns, about 200 microns to about 300 microns, or about 50 microns to about 250 microns). In some embodiments, OR-2 prime has an average bulk density of from about 0.75 g/mL to about 0.85 g/mL (e.g., about 0.75 g/mL, about 0.8, or about 0.85 g/mL). In some embodiments, OR-2 prime has an average surface area of from about 450 $m^2/g$ to about 500 $m^2/g$ (e.g., about 450 $m^2/g$ to about 490 $m^2/g$, about 450 $m^2/g$ to about 475 $m^2/g$, about 460 $m^2/g$ to about 500 $m^2/g$, or about 475 $m^2/g$ to about 500 $m^2/g$). In some embodiments, OR-2 prime has an average pore volume of from about 0.7 mL/g to about 0.9 mL/g (e.g., about 0.7 g/mL, about 0.75 g/mL, about 0.8 g/mL, about 0.85 g/mL, or about 0.9 g/mL). In certain embodiments of OR-2 prime resin, the modified hydrophobic adsorbent (i.e., hydrophobic resin) is a C18 resin.

OR-3 is a modified hydrophilic adsorbent comprising a spherical or irregular polar silica adsorbent having a high level of silanol (Si—O—H) groups. In some embodiments, OR-3 has an average particle diameter of from about 25 microns to about 300 microns (e.g., about 60 microns to about 300 microns, about 60 microns to about 200 microns, about 60 microns to about 150 microns, about 60 microns to about 100 microns, about 100 microns to about 200 microns, about 150 microns to about 200 microns, or about 100 microns to about 150 microns). In some embodiments, OR-3 has an average surface area of between about 350 m$^2$/g and 850 m$^2$/g (e.g., between about 350 m$^2$/g and 750 m$^2$/g, between about 450 m$^2$/g and 850 m$^2$/g, between about 450 m$^2$/g and 750 m$^2$/g, between about 450 m$^2$/g and about 550 m$^2$/g, between about 450 m$^2$/g to about 525 m$^2$/g, between about 450 m$^2$/g to about 500 m$^2$/g, between about 475 m$^2$/g to about 550 m$^2$/g, or between about 500 m$^2$/g to about 550 m$^2$/g), having an average pore volume of between 0.7 and 0.85 mL/g (e.g., about 0.7 g/mL, about 0.75 g/mL, about 0.8 g/mL, or about 0.85 g/mL). In certain embodiments, OR-3 has an average bulk density of about 0.4 g/mL to about 0.8 g/mL (e.g., about 0.5 g/mL to about 0.8 g/mL, about 0.6 g/mL to about 0.8 g/mL, about 0.4 g/mL to about 0.7 g/mL, about 0.4 g/mL to about 0.6 g/mL). In some embodiments, OR-3 has an average pore size of between about 40 Å and about 1000 Å (e.g., about 50 Å and 1000 Å, about 50 Å and 500 Å, about 50 Å and 250 Å, about 50 Å and 100 Å, or about 50 Å and 75 Å).

OR-4 is an activated alumina adsorbent. In some embodiments, OR-4 has an average particle diameter of from about 50 microns to about 200 microns (e.g., about 50 microns to about 150 microns, about 50 microns to about 100 microns, about 100 microns to about 200 microns, about 150 microns to about 200 microns, or about 100 microns to about 150 microns). In some embodiments, OR-4 has an average bulk density of between 0.7 g/mL and 0.85 g/mL (e.g., about 0.7 g/mL, about 0.75 g/mL, about 0.8 g/mL, or about 0.85 g/mL). In some embodiments, OR-4 has an average surface area of between 140-170 m$^2$/g, and an average pore diameter of greater than 60 Angstroms (i.e., greater than 0.006 microns).

OR-5 is a hydrophobic polystyrene-divinylbenzene adsorbent. In some embodiments, OR-5 has an average particle diameter of from about 250 microns to about 600 microns (e.g., about 250 microns to about 500 microns, about 250 microns to about 400 microns, about 250 microns to about 300 microns, about 300 microns to about 600 microns, about 400 microns to about 600 microns, about 500 microns to about 600 microns, or about 300 microns to about 500 microns). In some embodiments, OR-5 has an average bulk density of from about 0.6 g/mL to about 0.9 g/mL (e.g., about 0.6 g/mL, about 0.65 g/mL, about 0.7 g/mL, about 0.75 g/mL, about 0.8 g/mL, about 0.85 g/mL, or about 0.9 g/mL). In some embodiments, OR-5 has an average water content of from about 35% to about 65% (e.g., about 55% to about 65% or about 60%).

OR-5 prime (i.e., OR-5') is a hydrophobic divinylbenzene-based adsorbent (e.g., a polystyrene-divinylbenzene adsorbent, a polydivinylbenzene adsorbent, a macroporous polystyrene-divinylbenzene adsorbent, or a macroporous polydivinylbenzene adsorbent). In certain embodiments, OR-5 prime is a hydrophobic polystyrene-divinylbenzene adsorbent. In some embodiments, OR-5 prime has an average particle diameter range from 60 microns to 300 microns (e.g., about 60 microns to about 250 microns, about 60 microns to about 225 microns, or about 60 microns to about 200 microns). In some embodiments, OR-5 prime has an average bulk density of from about 0.6 g/mL to about 0.9 g/mL (e.g., about 0.6 g/mL, about 0.65 g/mL, about 0.7 g/mL, about 0.75 g/mL, about 0.8 g/mL, about 0.85 g/mL, or about 0.9 g/mL) or from about 0.65 g/mL to about 0.7 g/mL. In some embodiments, OR-5 prime has an average water content of from about 35% to about 80% (e.g., about 55% to about 80%, about 55% to about 70%, about 55% to about 67%, about 55% to about 65%, or about 65% to about 80%). In some embodiments, OR-5 prime has an average pore size of from about 75 Å to 550 Å (e.g., about 100 Å to about 550 Å, about 200 Å to about 550 Å, about 300 Å to about 550 Å, about 100 Å to about 500 Å, about 200 Å to about 500 Å, about 300 Å to about 500 Å, about 100 Å to about 400 Å, about 200 Å to about 400 Å, or about 300 Å to about 400 Å). In some embodiments, OR-5 prime has an average surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g, about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g). In some embodiments, OR-5 prime has a minimum surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g).

OR-11 is a hydrophobic divinylbenzene-based adsorbent (e.g., a polystyrene-divinylbenzene adsorbent, a polydivinylbenzene adsorbent, a macroporous polystyrene-divinylbenzene adsorbent, or a macroporous polydivinylbenzene adsorbent). In certain embodiments, OR-11 is a hydrophobic crosslinked divinylbenzene adsorbent. In some embodiments, OR-11 has an average particle diameter range from 20 microns to 200 microns (e.g., about 20 microns to about 160 microns, about 20 microns to about 120 microns, about 20 microns to about 100 microns, about 20 microns to about 80 microns, about 20 microns to about 60 microns, or about 60 microns to about 100 microns). In some embodiments, OR-11 has an average bulk density of from about 0.45 g/mL to about 0.9 g/mL (e.g., about 0.45 g/mL, about 0.5 g/mL, about 0.55 g/mL, about 0.65 g/mL, about 0.75 g/mL, about 0.8 g/mL, about 0.85 g/mL, or about 0.9 g/mL) or from about 0.45 g/mL to about 0.7 g/mL. In some embodiments, OR-11 has an average water content of from about 35% to about 80% (e.g., about 55% to about 80%, about 55% to about 70%, about 55% to about 67%, about 55% to about 65%, or about 65% to about 80%). In some embodiments, OR-11 has an average pore size of from about 75 Å to 550 Å (e.g., about 100 Å to about 550 Å, about 200 Å to about 550 Å, about 300 Å to about 550 Å, about 100 Å to about 500 Å, about 200 Å to about 500 Å, about 300 Å to about 500 Å, about 100 Å to about 400 Å, about 200 Å to about 400 Å, or about 300 Å to about 400 Å). In some embodiments, OR-11 has an average surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g, about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g). In some embodiments, OR-11 has a minimum surface area of from about 450 m$^2$/g to about 900 m$^2$/g (e.g., about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g).

Thus, as used herein, the phrase "hydrophobic divinylbenzene-based adsorbent" can refer to any polystyrene-divinylbenzene adsorbent, polydivinylbenzene adsorbent, macroporous polystyrene-divinylbenzene adsorbent, or macroporous polydivinylbenzene adsorbent having an average particle diameter of 20 microns to 600 microns, an average surface area of 450 m$^2$/g to 900 m$^2$/g, an average pore size of 75 Å to 550 Å, an average water content of from about 35% to about 80% (e.g., about 55% to about 80%), an average bulk density of 0.45 g/mL to 0.9 g/mL, or any combination thereof. In certain preferred embodiments, the hydrophobic divinylbenzene-based adsorbent has an average particle diameter of from 20 microns to 300 microns (e.g., about 20 microns to about 250 microns, about 20 microns to about 225 microns, or about 20 microns to about 200 microns). In particularly preferred embodiments, the hydrophobic divinylbenzene-based adsorbent has an average particle diameter of from 20 microns to 250 microns or from 20 microns to 225 microns.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter of from 250 microns to about 600 microns (e.g., about 300 microns to about 600 microns, about 400 microns to about 600 microns, about 500 microns to about 600 microns, or about 300 microns to about 500 microns average bulk density of from about 0.6 g/mL to about 0.9 g/mL, and an average water content of from about 35% to about 70% (e.g., about 35% to about 67%, about 55% to about 70%, or about 55% to about 67%).

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter of from 20 microns to 300 microns (e.g., about 20 microns to about 250 microns, about 20 microns to about 225 microns, or about 20 microns to about 200 microns), an average bulk density of from about 0.45 g/mL to about 0.7 g/mL, an average water content of from about 35% to about 70% (e.g., about 35% to about 67%, about 55% to about 70%, or about 55% to about 67%), and an average surface area of from about 550 m$^2$/g to about 600 m$^2$/g.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from 20 microns to 200 microns (e.g., about 20 microns to about 160 microns, about 20 microns to about 120 microns, about 20 microns to about 100 microns, about 20 microns to about 80 microns, or about 20 microns to about 60 microns), an average bulk density of from about 0.65 g/mL to about 0.7 g/mL, an average water content of from about 35% to about 70% (e.g., about 35% to about 67%, about 55% to about 70%, or about 55% to about 67%), and an average surface area of from about 550 m$^2$/g to about 600 m$^2$/g.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from about 20 microns to about 200 microns (e.g., about 20 microns to about 60 microns or about 60 microns to about 100 microns), an average pore size of from about 300 Å to 500 Å, an average water content of from about 35% to about 80% (e.g., about 55% to about 80%), and an average surface area of from about 550 m$^2$/g to about 650 m$^2$/g.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from about 20 microns to about 200 microns (e.g., e.g., about 20 microns to about 120 microns, about 20 microns to about 60 microns or about 60 microns to about 120 microns), an average pore size of from about 200 Å to about 400 Å, and an average surface area of from about 600 m$^2$/g to about 800 m$^2$/g.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from 60 microns to 300 microns (e.g., about 60 microns to about 250 microns, about 60 microns to about 225 microns, or about 60 microns to about 200 microns), an average pore size of from about 200 Å to about 400 Å, and an average surface area of from about 600 m$^2$/g to about 800 m$^2$/g.

Typically, the chromatographic resin is contained in a container (e.g., a column). The container can be any suitable container. Generally the container is a column. The chromatographic resin can be in a single column, or in more than one column (e.g., two or more columns, three or more columns, four or more columns, five or more columns, six or more columns, seven or more columns, eight or more columns, nine or more columns, or ten or more columns). In some embodiments, the chromatographic resin is in a single column. In some embodiments, the chromatographic resin is in more than one column.

In some embodiments where the chromatographic resin is in more than one column, at least a portion of the more than one column can be arranged in an SMB configuration. Accordingly, the feedstock stream can be purified and/or processed and purified by an SMB chromatographic method described herein. In some embodiments, where the chromatographic resin is in more than one column, at least a portion of the more than one column can be arranged in series (e.g., a batch column chromatography configuration). For example, batch column chromatography can be utilized to produce an increased yield of a cannabinoid and increase the longevity of a chromatographic resin. The process reuses a chromatographic resin in another stage of the purification process to obtain more of the cannabinoid and to increase the utility of the chromatographic resin.

In some embodiments, the chromatographic resins described herein can be flushed with a solvent (e.g., ethanol) to recover the cannabinoid. In some embodiments, the chromatographic resins described herein can be regenerated for use in subsequent separation cycles. As used herein, "regeneration" can refer to the process of washing the resin with a regeneration solution to remove THC/THCA, additional impurities, or cannabinoids. The chromatographic resins (e.g., OR-2, OR-2 prime, OR-5, OR-5 prime, and/or OR-11) can be regenerated using any suitable regeneration solution. For example, the regeneration solution can comprise ethanol, acetone, ethyl acetate, acetonitrile, pentanes, hexanes, heptanes, methanol, isopropyl alcohol, propanol, and a combination thereof. It will be readily understood to a skilled artisan which solution will be particularly preferable for each resin described herein. The regeneration solution of some embodiments comprises less than 5 wt % water, and includes ethanol, acetone, or a combination thereof. In preferred embodiments, the regeneration solution comprises acetone.

The methods of the disclosure utilize a mobile phase desorbent ("mobile phase") or solvent to elute the at least one cannabinoid and/or THC/THCA from the stationary phase. The mobile phase (e.g., solvent) can be any suitable mobile phase capable of eluting a constituent. For example, the mobile phase (e.g., solvent) can comprise water, ethanol, acetone, ethyl acetate, acetonitrile, pentanes, hexanes, heptanes, methanol, isopropyl alcohol, propanol, or a combination thereof. In certain embodiments, the mobile phase desorbent (e.g., solvent) for use in the methods described herein (e.g., SMB and batch chromatography) is pure ethanol (e.g., greater than 97% ethanol, greater than 98% ethanol, or greater than 99% ethanol). In some embodiments, a mobile phase desorbent (e.g., solvent) for use in the methods described herein (e.g., SMB and batch chromatography) is a mixture of ethanol (e.g., food grade ethanol) and water (e.g., deionized water), or in other words, an ethanolic mixture. As used herein, the term "ethanolic" can mean comprising ethanol. The mobile phase desorbent (e.g., solvent) can employ a ratio of ethanol to water of from about 50 parts ethanol (Food grade ethanol—200 Proof) to about 50 parts water to about 90 parts ethanol to about 10 parts water (i.e., a ratio of ethanol to water of about 50:50, about 55:45, about 60:40, about 65:35, about 70:30, about 75:25, about 80:20, about 85:15, or about 90:10). In some embodiments, the mobile phase desorbent (e.g., solvent) employs a ratio of ethanol to water of from about 50 parts ethanol to about 50 parts water to about 80 parts ethanol to about 20 parts water. In certain embodiments, the ratio of ethanol to water in the mobile phase (e.g., solvent) is about 80 parts ethanol to about 20 parts water. The mobile phase desorbent (e.g., solvent) can employ any suitable ratio of ethanol to heptanes, e.g., of from about 5 parts ethanol (Food grade ethanol—200 Proof) to about 95 parts heptanes to about 95 parts ethanol to about 5 parts heptanes (i.e., a ratio of ethanol to heptanes of about 10:90, about 20:80, about 30:70, about 40:60, about 50:50, about 55:45, about 60:40, about 65:35, about 70:30, about 75:25, about 80:20, about 85:15, or about 90:10).

At any step in the methods described herein, at least a portion of the solvent can optionally be removed to form a concentration stream. Thus, in some embodiments, the method further comprises removing the solvent to provide a reduced version of the stream (e.g., a primary raffinate, an extract stream, a feedstock stream, etc.). The solvent can be removed by any suitable method. For example, the solvent can be removed by evaporation (e.g., under reduced pressure, elevated temperature, or a combination thereof), membrane permeation (e.g., nano-filtration), or a combination thereof. Such a concentration step can be useful to perform, for example, sample analysis, purification solvent swaps, and/or concentration adjustments.

The methods of the disclosure remove THC and/or THCA from a mixture. The mixture can be prepared by any suitable method or obtained from any suitable source such that it contains at least one cannabinoid to be separated (i.e., purified) from THC and/or THCA. In some embodiments, the mixture is extracted from dried hemp or cannabis leaves with a solvent. An exemplary procedure for extracting the mixture from dried hemp or cannabis leaves is as follows. Following harvesting and processing, the grinded and dried hemp or cannabis leaves are extracted with an appropriate GRAS solvent, preferably ethanol, or mixtures of ethanol and water. A number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material:solvent (v/v)) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results. The extracted mixture (e.g., the hemp or cannabis leave extract) can be used directly as a feedstock stream or can be filtered or diluted with additional solvent to provide a feedstock stream.

An exemplary process for extracting crude cannabis from dry hemp leaves is as follows:
  i) combining dry hemp leaves with a first portion of food grade ethanol to provide a first leaf/solvent mixture and agitating the first leaf/solvent mixture;
  ii) soaking the first leaf/solvent mixture for an effective soaking time to form a first ethanol layer;
  iii) decanting the first ethanol layer to provide a first decant stream and a first portion of wet leaves;
  iv) combining a second portion of food grade ethanol with the first portion of wet leaves to provide a second leaf/solvent mixture and agitating the second leaf/solvent mixture and decanting a second ethanol layer to provide a second decant stream and residual leaves; and,
  v) pressing the residual leaves to provide a third decant stream and combining the first decant stream, the second decant stream and the third decant streams to provide the crude cannabis extract stream.

The leaf extraction process can be carried out at atmospheric pressure and room temperature of about 25° C. The first leaf mixture is allowed to soak for an effective soaking time comprising about 8 to 12 hours. Preferably, the combined decant streams should have a solids/oils concentration of between about 23 to about 30 g/Liter. More preferably the combined decant streams should have a maximum solids/oils concentration less than about 30 g/Liter.

In some embodiments, the mixture is hemp extract (i.e., non-decolorized and non-decarboxylated hemp extract). As used herein, the phrase "hemp extract" can refer to a mixture prepared by using ethanol solvent to extract the desired compounds from industrial hemp leaves. In some embodiments, the hemp extract is further mixed with water to form an ethanol/water mixture. The resulting ethanol/water mixture comprising hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In some embodiments, the mixture is decolorized hemp extract (i.e., decolorized and non-decarboxylated hemp extract). As used herein, the phrase "decolorized hemp extract" can refer to a mixture prepared by using ethanol solvent to extract the desired compounds from industrial hemp leaves. The resulting extract is then processed through a chromatographic resin (e.g., OR-1) to decolorize (i.e., remove chlorophylls & pigments). In some embodiments, the decolorized hemp extract is further mixed with water to form an ethanol/water mixture. The resulting ethanol/water mixture comprising decolorized hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In certain embodiments, the mixture is decarboxylated hemp extract (i.e., decarboxylated and non-decolorized hemp extract. As used herein, the phrase "decarboxylated hemp extract" can refer to a mixture that is prepared by using ethanol solvent to extract the desired compounds from industrial hemp leaves. The resulting extract is then placed in a still to apply heat to activate/convert the acidic form to a decarboxylated form. In some embodiments, the decarboxylated hemp extract is further mixed with water to form an ethanol/water mixture. The resulting ethanol/water mixture comprising decarboxylated hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In certain embodiments, the mixture is decolorized and decarboxylated hemp extract. As used herein, the phrase "decolorized and decarboxylated hemp extract" can refer to a mixture that is prepared by using ethanol solvent to extract the desired compounds from industrial hemp leaves. The resulting extract is then processed through a chromatographic resin (e.g., OR-1) to decolorize (i.e., remove chlorophylls & pigments). The decolorized hemp extract is then placed in a still to apply heat to activate/convert the acidic form to a decarboxylated form. In some embodiments, the decolorized and decarboxylated hemp extract is further mixed with water to form an ethanol/water mixture. The resulting ethanol/water mixture comprising decolorized and decarboxylated hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

The mixture can be purified by any suitable chromatography method or combination of chromatography methods. For example, the mixture can be purified by single column chromatography, batch column chromatography, or simulated moving bed (SMB) chromatography. In embodiments, single column chromatography comprises a purification process in which the composition is passed through a single stationary phase contained in a single container. In embodiments, batch column chromatography comprises a purification process in which the composition is passed through one or more stationary phases contained in more than one container, such as by the methods described in U.S. Patent Application Publication No. 2019/0010110 A1. U.S. Pat. No. 2,985,589 describes a simulated moving bed (SMB) chromatography technique in which a chromatography system involving a separation tower is divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow.

The methods described herein utilize a simulated moving bed (SMB) system for at least one purification step. In some embodiments, the simulated moving bed (SMB) system is arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. Feed and mobile phase desorbent enter, while extract and raffinate streams are withdrawn continuously or semi-continuously. The overall operation is similar in performance to an operation wherein the fluid and solid are contacted in a continuous countercurrent manner, without the actual movement of the solid, or stationary phase adsorbent.

The SMB system can be operated in any suitable format (e.g., sequential SMB format). For example, the SMB system may be operated such that the adsorbent beds are operated individually or in parallel using a single rotary valve and associated control system. A column may comprise one or more beds containing chromatographic media. Associated feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art. In some embodiments, the SMB system is operated in sequential SMB format. As used herein, "sequential SMB format refers to an SMB process where multiple mobile phase compositions, multiple flow rates, multiple step times, or a combination thereof are utilized to increase separation. In some embodiments, the SMB system is not operated in sequential SMB format, i.e., a single mobile phase composition, a single flow rate, and a single step time is used.

The methods described herein comprise passing a feedstock stream through a chromatographic resin arranged in a simulated moving bed (SMB) chromatography configuration to provide a primary raffinate stream and an SMB extract stream. The SMB chromatography configuration comprises a plurality of adsorbent beds (e.g., columns comprising a stationary phase). The SMB chromatography configuration can comprises any suitable number of adsorbent beds. For example, the SMB chromatography configuration can comprise 2 or more adsorbent bed, e.g., 3 or more adsorbent beds, 4 or more adsorbent beds, 5 or more adsorbent beds, 6 or more adsorbent beds, 10 or more adsorbent beds, or 20 or more adsorbent beds. In some embodiments, the plurality of adsorbent beds are arranged in serial fluid communication such that fluid introduced at a top of any adsorbent bed (n) passes to the next highest adsorbent bed (n+1). In such embodiments, the method can further comprise advancing each adsorbent bed, such that adsorbent bed n+1 becomes adsorbent bed n after advancing, and adsorbent bed n prior to advancing becomes adsorbent bed n+x after advancing, wherein adsorbent bed n+x is the highest adsorbent bed in the serial fluid communication arrangement.

Figure 6:
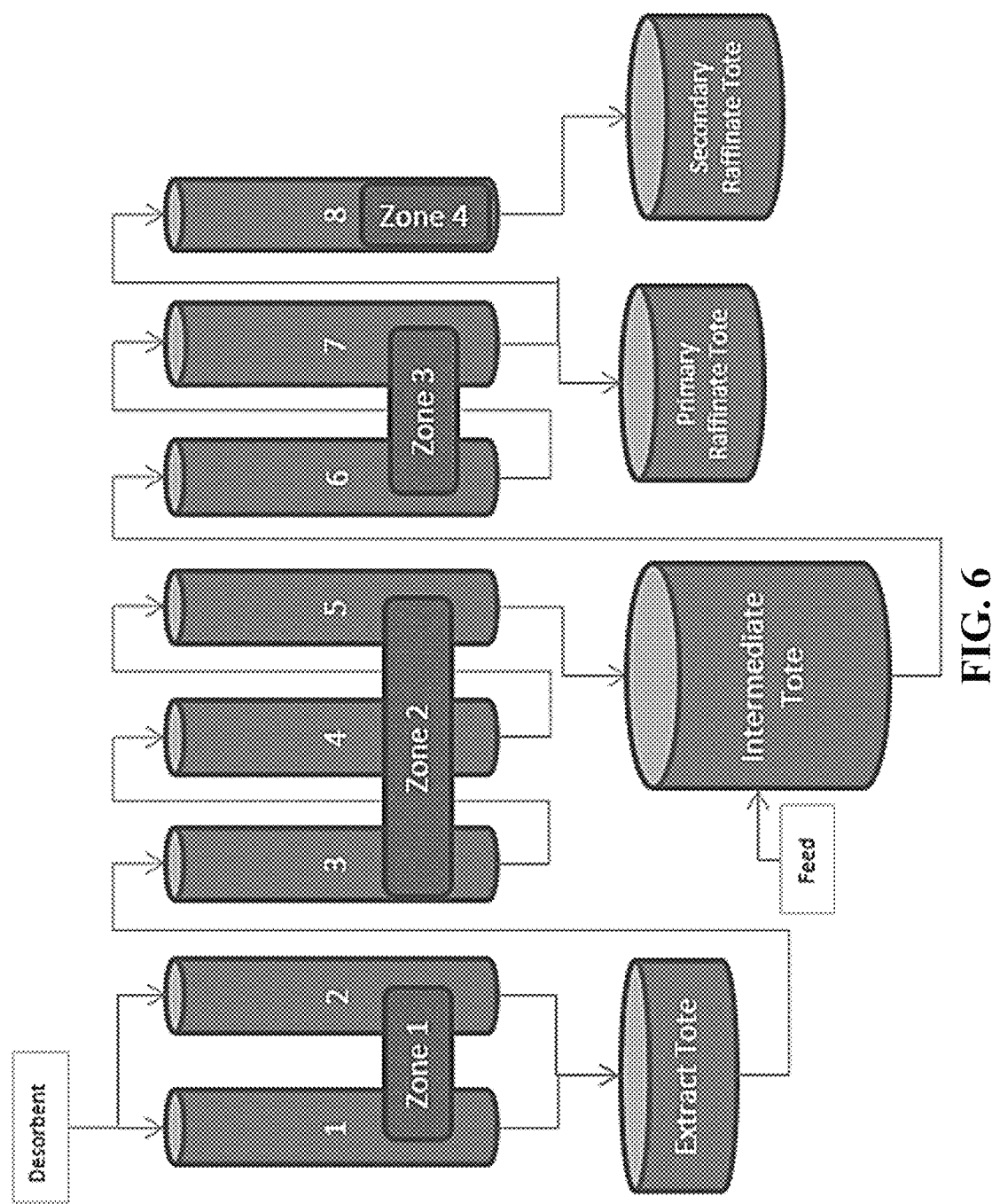
FIG. 6 is a schematic diagram depicting an SMB zone (i.e., a SMB configuration) in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a concentration zone, respectively.

In some embodiments, the SMB zone chromatography configuration comprises eight adsorbent beds. The eight adsorbent beds can be broken down into four zones referring to a desorption zone, a rectification zone, an adsorption zone, and a concentration zone. The adsorbent beds can be in any suitable arrangement (e.g., 2-2-2-2, 3-2-2-1, 2-3-2-1, 2-2-3-1, 1-3-3-1, 3-3-1-1, 3-1-3-1, or 2-2-3-1, etc.), wherein each number refers to one of the four zones. In certain embodiments, the SMB chromatography configuration is in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a concentration zone, respectively. Such an arrangement is depicted in FIG. 6.

According to one embodiment of the disclosure and with reference to FIG. 1, the simulated moving bed system is a continuous simulated moving bed system which continuously processes the feedstock stream in line 10 to provide a primary raffinate stream in line 36. There were eight adsorption beds arranged in series and connected through a proprietary pneumatic valve array (not shown). The SMB scheme shown in FIG. 1 is a 2-3-2-1 arrangement, wherein 2 adsorbent beds (C-1, C-2) were operated in a desorption zone, 3 adsorbent beds (C-3, C-4, C-5) were operated in a rectification zone, 2 adsorbent beds (C-6, C-7) were operated in an adsorption zone, and 1 adsorbent bed (C-8) was operated in a concentration zone for raffinate. The independently working and programmable 72-valve array contains no moving parts, occupies only 3 µl per valve, and responds within 100 ms. Fluid flow is controlled by four independent pumps. The valve switching and pump flow rates are controlled via the SembaPro Software. The eight adsorbent beds (C-1, C-2, C-3, C-3, C-4, C-5, C-6, C-7, and C-8) were cylinders of 304 stainless steel, each adsorbent bed having an inside column diameter of 15 cm (6 inch) and a column length of 90 cm (36 inches), and each adsorbent bed contained about 10 Kg of OR2 adsorbent. The rotary valve system was operated on a cycle, wherein bed switching occurred at every 10-20 minute intervals. The eight adsorption beds were arranged in serial fluid communication such that fluid introduced at the top of any adsorbent bed n continued to the next highest adsorbent bed n+1 by passing the effluent from the bottom of adsorbent bed n to the top of adsorbent bed n+1. The adsorbent beds were operated in four zones, zone 1 (desorption), zone 2 (rectification), zone 3 (adsorption), and zone 4 (concentration), whereby the SMB feedstock stream in line 40 was loaded on to zone 3 (C-6) by introducing the SMB feedstock stream via lines 40 and 28 to adsorbent bed C-6. In zone 3, the cannabinoid was selectively adsorbed in adsorbent beds C-6 and C-7, and the primary raffinate stream was withdrawn in lines 32 and 36 from adsorbent bed C-7. The primary raffinate in line 68 can be passed to an evaporation zone (not shown) to recover the solvent; and, following evaporation of the primary raffinate stream to dryness, provides a high purity cannabinoid which is essentially free of THC. At least a portion of the primary raffinate steam in line 32 was passed to zone 4 comprising adsorbent bed C-8 in line 34 and a secondary raffinate stream was withdrawn from adsorbent bed C-8 in line 38. The secondary raffinate is withdrawn in line 38 at a very small flow rate compared to the flow rate of the primary raffinate flow rate and comprises essentially no cannabinoid or THC oils. The secondary raffinate stream can be directly returned to zone 1 to offset the amount of the mobile phase desorbent in line 10. In the same step, a polar mobile phase desorbent in line 10, comprising an 80:20 volume mixture of ethanol and water, was simultaneously introduced to zone 1, comprising adsorbent beds C-1 and C-2, via lines 12 and 14, respectively. The mobile phase was passed through zone 1 in parallel through adsorbent beds C-1 and C-2, and the effluent of adsorbent beds C-1 and C-2 was withdrawn in lines 16 and 18, respectively, and combined to form an SMB extract stream in line 20. The SMB extract stream line 20 is passed to a second evaporation zone for solvent recovery (not shown). A portion of the SMB extract stream in line 22 was passed to zone 2 (comprising adsorbent beds C-3, C-4, and C-5) and introduced to the top of adsorbent bed C-3, and continuing serially through adsorbent beds C-3, C-4, and C-5 via lines 24, and 26, respectively. The effluent withdrawn from the bottom of adsorbent bed C-5 was passed to the top of adsorbent bed C-6 in line 27, and admixed with the SMB feedstock stream in line 40 before being passed to adsorbent bed C-6 in line 28. At the completion of each SMB cycle, the adsorbent beds was advanced to move countercurrent to the SMB feedstock, whereby adsorbent bed C-2 shifts to the left to the position previously occupied by C-1 and C-1 was shifted to the position previously occupied by adsorbent bed C-8.

The adsorbent beds of the SMB chromatography configuration can comprise the same stationary phase or different stationary phases. In preferred embodiments, the adsorbent beds of the SMB chromatography configuration comprise the same stationary phase. For example, the adsorbent beds can comprise OR-1, OR-2, OR-2 prime, OR-3, OR-4, OR-5, OR-5 prime, and/or OR-11. In various embodiments, the SMB chromatography configuration comprises a plurality of adsorbent beds, each bed containing OR-1; OR-2; OR-2 prime; OR-3; OR-5; OR-5 prime; or OR-11.

In embodiments, OR-5 can be used in a SMB technology system. The OR-5 SMB technology system can be used for THC and/or THCA removal from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions are THCA and THC free (e.g., undetectable amounts of THCA and THC). After a specific number of bed volumes, the capacity of this single guard bed column for THCA and THC retention is exceeded. However, this guard bed column can still be utilized for reduction in Wax impurities. The effluent from the guard bed is then passed onto the OR-5 SMB chromatography configuration as feed liquid. Processing the effluent from the single column through SMB technology further purifies CBD and CBDA. OR-5 stationary phase is regenerated using an ethanolic mixture for continuous, repeatable chromatographic separation.

In embodiments, OR-5 can be used in a SMB technology system. OR-5 adsorbent in SMB technology can remove THC from decolorized and decarboxylated hemp extract. Decolorized and decarboxylated hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THC free (e.g., undetectable amounts of THC). After a specific number of bed volumes, the capacity of this single guard bed column for THC retention is exceeded. However, this guard bed column can still be utilized for reduction in Wax impurities. The effluent from the guard bed is then passed onto the OR-5 SMB chromatography configuration as feed liquid. Processing the effluent from the single column through SMB technology further purifies CBD. OR-5 stationary phase is regenerated using an ethanolic mixture for continuous, repeatable chromatographic separation.

In embodiments, OR-5 can be used in a SMB technology system. OR-5 adsorbent in SMB technology can remove THCA from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THCA free. After a specific number of bed volumes, the capacity of this single guard bed column for THCA retention is exceeded. However, this guard bed column can still be utilized for reduction in Wax impurities. The effluent from the guard bed is then passed onto the OR-5 SMB chromatography configuration as feed liquid. Processing the effluent from the single column through SMB technology further purifies CBDA. OR-5 stationary phase is regenerated using an ethanolic mixture for continuous, repeatable chromatographic separation.

In embodiments, OR-5 prime can be used in a SMB technology system. The OR-5 SMB prime technology system can be used for THC and/or THCA removal from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions are THCA and THC free (e.g., undetectable amounts of THCA and THC). After a specific number of bed volumes, the capacity of this single guard bed column for THCA and THC retention is exceeded. However, this guard bed column can still be utilized for reduction in Wax impurities. The effluent from the guard bed is then passed onto the OR-5 prime SMB chromatography configuration as feed liquid. Processing the effluent from the single column through SMB technology further purifies CBD and CBDA. OR-5 prime stationary phase is regenerated using an ethanolic mixture for continuous, repeatable chromatographic separation.

In embodiments, OR-5 prime can be used in a SMB technology system. OR-5 prime adsorbent in SMB technology can remove THC from decolorized and decarboxylated hemp extract. Decolorized and decarboxylated hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THC free (e.g., undetectable amounts of THC). After a specific number of bed volumes, the capacity of this single guard bed column for THC retention is exceeded. However, this guard bed column can still be utilized for reduction in Wax impurities. The effluent from the guard bed is then passed onto the OR-5 prime SMB chromatography configuration as feed liquid. Processing the effluent from the single column through SMB technology further purifies CBD. OR-5 prime stationary phase is regenerated using an ethanolic mixture for continuous, repeatable chromatographic separation.

In embodiments, OR-5 prime can be used in a SMB technology system. OR-5 prime adsorbent in SMB technology can remove THCA from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THCA free. After a specific number of bed volumes, the capacity of this single guard bed column for THCA retention is exceeded. However, this guard bed column can still be utilized for reduction in Wax impurities. The effluent from the guard bed is then passed onto the OR-5 prime SMB chromatography configuration as feed liquid. Processing the effluent from the single column through SMB technology further purifies CBDA. OR-5 prime stationary phase is regenerated using an ethanolic mixture for continuous, repeatable chromatographic separation.

In embodiments, OR-11 can be used in a SMB technology system. The OR-11 SMB technology system can be used for THC and/or THCA removal from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions are THCA and THC free (e.g., undetectable amounts of THCA and THC). After a specific number of bed volumes, the capacity of this single guard bed column for THCA and THC retention is exceeded. However, this guard bed column can still be utilized for reduction in Wax impurities. The effluent from the guard bed is then passed onto the OR-11 SMB chromatography configuration as feed liquid. Processing the effluent from the single column through SMB technology further purifies CBD and CBDA. OR-11 stationary phase is regenerated using an ethanolic mixture for continuous, repeatable chromatographic separation.

In embodiments, OR-11 can be used in a SMB technology system. OR-11 adsorbent in SMB technology can remove THC from decolorized and decarboxylated hemp extract. Decolorized and decarboxylated hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THC free (e.g., undetectable amounts of THC). After a specific number of bed volumes, the capacity of this single guard bed column for THC retention is exceeded. However, this guard bed column can still be utilized for reduction in Wax impurities. The effluent from the guard bed is then passed onto the OR-11 SMB chromatography configuration as feed liquid. Processing the effluent from the single column through SMB technology further purifies CBD. OR-11 stationary phase is regenerated using an ethanolic mixture for continuous, repeatable chromatographic separation.

In embodiments, OR-11 can be used in a SMB technology system. OR-11 adsorbent in SMB technology can remove THCA from decolorized hemp extract. Decolorized hemp extract used as feed liquid is processed through a single column (e.g., OR-1, OR-2, OR-2 prime, OR-3, OR-4, OR-5, OR-5 prime, and/or OR-11) acting as a guard bed. The initial effluent fractions will be THCA free. After a specific number of bed volumes, the capacity of this single guard bed column for THCA retention is exceeded. However, this guard bed column can still be utilized for reduction in Wax impurities. The effluent from the guard bed is then passed onto the OR-11 SMB chromatography configuration as feed liquid. Processing the effluent from the single column through SMB technology further purifies CBD. OR-11 stationary phase is regenerated using an ethanolic mixture for continuous, repeatable chromatographic separation.

In embodiments, OR-3 can be used in a SMB technology system. OR-3 adsorbent in SMB technology can remove THC from an SMB extract stream. Processing the SMB extract stream from a previous SMB chromatography configuration (e.g., OR-5, OR-5 prime, and/or OR-11) through an OR-3 SMB chromatography configuration further purifies CBC. OR-3 stationary phase is regenerated using an ethanolic mixture for continuous, repeatable chromatographic separation.

In some embodiments, the methods described herein utilize a chromatographic resin that is disposed in a single column or more than one column in series (e.g., single column chromatography or batch column chromatography). Thus, any of the resins described herein (e.g., OR-1, OR-2, OR-2 prime, OR-3, OR-4, OR-5, OR-5 prime, and/or OR-11) can be used for single column chromatography or batch column chromatography.

In embodiments, OR-1 adsorbent can be used as a single column before and/or after an SMB chromatography configuration. The OR-1 single column can be used for THC/THCA removal and/or decolorization. For example, a hemp extract can be processed through a single column with OR-1 adsorbent to enrich CBD/CBDA with the removal of THC and/or THCA as well as Lipids and Waxes. Once the THC and THCA adsorption limit levels on the OR-1 stationary phase have been exceeded, the purification process is stopped. This CBD/CBDA material can then be decarboxylated, and the ethanol solvent can be removed.

In embodiments, OR-1 adsorbent can be used in batch column chromatographic before and/or after SMB chromatography configuration. OR-1 adsorbent can be used in batch chromatographic mode operations for removal of THC along with other impurities like non-polar Waxes/Lipids, and Color pigments. The batch column chromatography method utilizes a single column in various positions for multiple streams of impurity reduction. The identified stationary phase that is favorable for the batch column method has the capability to remove the THC, Wax, and Colored pigment impurity streams. Furthermore, this stationary phase exhibits an affinity for retention of specific impurity streams based on its (the stationary phase) level of saturation from incoming feed liquid. The level of saturation can be determined based on the volume of the stationary phase bed that has been packed into a chromatography column, and the volume of feed liquid that has been passed through that bed. The result is a purified cannabinoid output liquid that is free of THC. The batch mode of this chromatography sequence allows for increased recovery of a cannabinoid lost between successive steps.

In embodiments, OR-3 adsorbent can be used as a single column before and/or after an SMB chromatography configuration. The OR-3 single column can be used for THC/THCA removal. For example, a SMB extract stream can be processed through a single column with OR-3 adsorbent to enrich CBC with the removal of THC and/or THCA as well as Lipids and Waxes. Once the THC and THCA adsorption limit levels on the OR-3 stationary phase have been exceeded, the purification process is stopped.

In embodiments, OR-3 adsorbent can be used in batch column chromatographic before and/or after SMB chromatography configuration. OR-3 adsorbent can be used in batch chromatographic mode operations for removal of THC/THCA along with other impurities like non-polar Waxes/Lipids, and Color pigments. The process can result in highly enriched cannabinoids such as CBC.

In some embodiments, the methods described herein provide an isolated yield (i.e., a percent recovery) of at least about 50% or more (e.g., at least about 55% or more, at least about 60% or more, at least about 65% or more, at least about 70% or more, at least about 80% or more, at least about 85% or more, at least about 90% or more, or at least about 95% or more) of the cannabinoid. In preferred embodiments, the methods described herein provide an isolated yield of from about 75% to about 100% (e.g., about 75% to about 90%, about 75% to about 85%, about 80% to about 100%, about 80% to about 90%, about 85% to about 100%, or about 85% to about 90%) of the cannabinoid.

In some embodiments, the methods described herein provide a level of THC of less than about 0.3 wt % (e.g., less than about 0.2 wt %, less than about 0.1 wt %, trace amounts, or no detectable amount) on a solvent free basis. In certain embodiments, the methods described herein provide a trace amount of THC on a solvent free basis. As used herein, the phrase "trace amount" refers to less than about 0.01 wt % on a solvent free basis. In preferred embodiments, the methods described herein provide no detectable amount of THC on a solvent free basis. Thus, as used herein, the term "THC free" can refer to a level of THC of less than about 0.3 wt % (e.g., less than about 0.2 wt %, less than about 0.1 wt %, trace amounts, or no detectable amount) on a solvent free basis. In certain embodiments, THC free refers to no detectable amount of THC.

The method of some embodiments further comprises cooling the isolate stream to form a crystallized cannabinoid. The cannabinoid can be crystallized by any suitable method and to any suitable purity. In some embodiments, the method comprises cooling the isolate elute stream for a cooling period of time, to thereafter provide crystallized cannabinoid. The crystallized cannabinoid can have a purity of from about 90 wt % to about 100 wt % (e.g., about 92 wt % to about 99 wt %, about 95 wt % to about 99 wt %, or about 96 wt % to about 98 wt %) as determined by HPLC. In certain embodiments, the crystallized cannabinoid has a purity of from about 96 wt % to about 98 wt % as determined by HPLC. In some embodiments, the method further comprises recrystallizing the crystallized cannabinoid. The crystallized cannabinoid can be recrystallized by any suitable method and to any suitable purity. For example, the recrystallized cannabinoid can have a purity of from about 95 wt % to about 100 wt % (e.g., about 96 wt % to about 100 wt %, about 97 wt % to about 100 wt %, about 98 wt % to about 100 wt %, or about 99 wt % to about 100 wt %). In certain embodiments, the recrystallized cannabinoid has a purity of greater than about 99 wt % as determined by HPLC.

Figure 7:
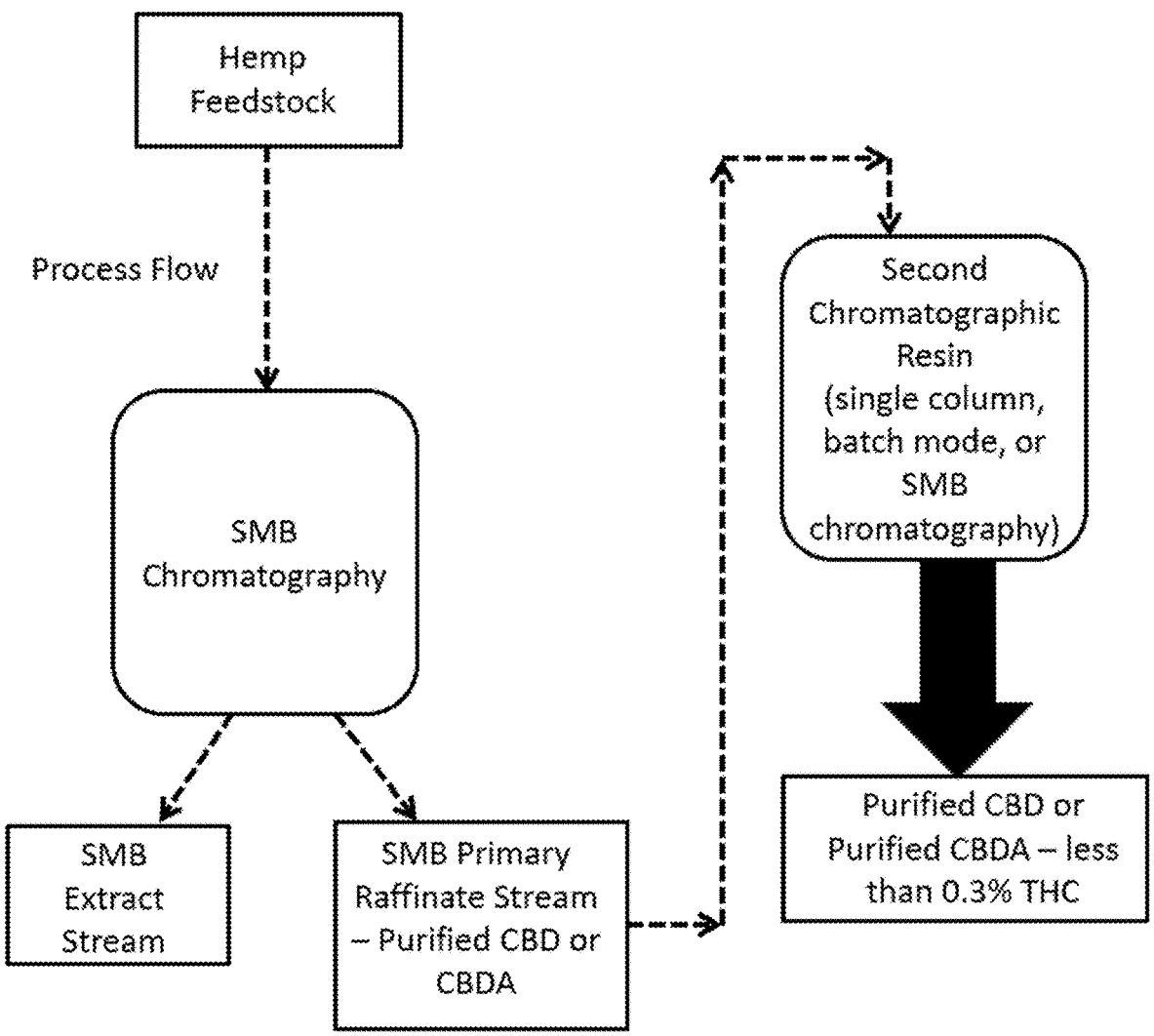
FIG. 7 is a schematic depicting the first illustrative aspect of the present disclosure.

In a first illustrative aspect of the disclosure, as depicted in FIG. 7, provided is a method of removing THC and/or THCA from a mixture, the mixture including THC and/or THCA and at least one cannabinoid, the method comprising preparing a first feedstock stream from the mixture, the first feedstock stream comprising THC and/or THCA, at least one cannabinoid (e.g., cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof), and a first solvent; passing the first feedstock stream through a first chromatographic resin arranged in a simulated moving bed (SMB) chromatography configuration to provide a primary raffinate stream and an SMB extract stream, the primary raffinate stream having less than 0.9 wt % THC (e.g., less than 0.8 wt % THC, less than 0.75 wt % THC, or less than 0.5 wt % THC) on a solvent free basis and optionally a higher weight percentage of at least one cannabinoid than in the first feedstock stream on a solvent free basis; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent and the second feedstock stream having less than 0.9 wt % THC (e.g., less than 0.8 wt % THC, less than 0.75 wt % THC, or less than 0.5 wt % THC) on a solvent free basis; and passing the second feedstock stream through a second chromatographic resin to provide an eluate stream, the eluate stream having less than 0.3 wt % THC (e.g., less than 0.2 wt %, less than 0.1 wt %, trace amounts, or not detectable amount) on a solvent free basis and optionally a higher weight percentage of at least one cannabinoid than in the second feedstock stream on a solvent free basis.

In the first illustrative aspect of the disclosure, the at least one cannabinoid can be any suitable cannabinoid described herein (e.g., cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof). However, in preferred embodiments of the first illustrative aspect of the disclosure, the at least one cannabinoid is cannabidiol (CBD), cannabidiolic acid (CBDA), or a mixture thereof.

Also in the first illustrative aspect of the disclosure, the first chromatographic resin and the second chromatographic resin are each independently selected from: (i) an activated carbon adsorbent, (ii) a silica adsorbent, (iii) a hydrophobic divinylbenzene-based adsorbent, (iv) an activated alumina adsorbent, (v) a reverse phase carbon-based adsorbent, and (vi) a combination thereof, as described herein. For example, the first chromatographic resin and the second chromatographic resin are each independently selected from (e.g., OR-1, OR-2, OR-2 prime, OR-3, OR-4, OR-5, OR-5 prime, and/or OR-11). In preferred embodiments of the first illustrative aspect of the disclosure, the first chromatographic resin is a hydrophobic divinylbenzene-based adsorbent (e.g., OR-5, OR-5 prime, and/or OR-11) and/or the second chromatographic resin is an activated carbon adsorbent (e.g., OR-1).

In the first illustrative aspect of the disclosure, the first chromatographic resin arranged in a simulated moving bed (SMB) chromatography configuration and the second chromatographic resin can be disposed in a single column or more than one column in series. Thus the second chromatographic resin can be used in single column chromatography, batch column chromatography, or SMB chromatography. In a preferred embodiments of the first illustrative aspect of the disclosure, the second chromatographic resin is used in batch column chromatography.

In the first illustrative aspect of the disclosure, the method can comprise regenerating the first chromatographic resin by washing the first chromatographic resin with a first regeneration solution to produce a first wash and/or regenerating the second chromatographic resin by washing the second chromatographic resin with a second regeneration solution to produce a second wash. In some embodiments, the solvent can be removed from the first wash and/or the second wash and the concentrated first wash or concentrated second wash can be used in subsequent steps in the process.

The first illustrative aspect of the disclosure utilizes a first chromatographic resin arranged in a simulated moving bed (SMB) chromatography to obtain a primary raffinate stream having less than 0.9 wt % THC (e.g., less than 0.8 wt % THC, less than 0.75 wt % THC, or less than 0.5 wt % THC) on a solvent free basis, which can be used as the second feedstock stream for the second chromatographic resin. Without wishing to be bound by any particular theory, it is believed that the reduced weight percentage of THC upon purification with the second feedstock stream provides a more effective purification process, which produces an increased amount (i.e., bed volumes) of THC product. In other words, when the THC level in the primary raffinate and second feedstock stream is greater than 0.9 wt %, the second chromatographic resin becomes exhausted at an accelerated rate. Thus, in the first illustrative aspect of the disclosure, the THC level in the primary raffinate and second feedstock stream is less than 0.9 wt % on a solvent free basis, and preferably less than 0.8 wt % on a solvent free basis, and more preferably less than 0.75 wt % on a solvent free basis.

Thus, in a preferred embodiment of the first illustrative aspect, disclosure provides a method of removing THC and/or THCA from a mixture, the mixture including THC and/or THCA and CBD and/or CBDA, the method comprising preparing a first feedstock stream from the mixture, the first feedstock stream comprising THC and/or THCA, CBD and/or CBDA, and a first solvent; passing the first feedstock stream through a hydrophobic divinylbenzene-based adsorbent arranged in a simulated moving bed (SMB) chromatography configuration to provide a primary raffinate stream and an SMB extract stream, the primary raffinate stream having less than 0.9 wt % THC (e.g., less than 0.8 wt % THC, less than 0.75 wt % THC, or less than 0.5 wt % THC) on a solvent free basis and a higher weight percentage of CBD and/or CBDA than in the first feedstock stream on a solvent free basis; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent and the second feedstock stream having less than 0.9 wt % THC (e.g., less than 0.8 wt % THC, less than 0.75 wt % THC, or less than 0.5 wt % THC) on a solvent free basis; and passing the second feedstock stream through an activated carbon adsorbent to provide an eluate stream, the eluate stream having less than 0.3 wt % THC (e.g., less than 0.2 wt %, less than 0.1 wt %, trace amounts, or not detectable amount) on a solvent free basis and a higher weight percentage of CBD and/or CBDA than in the second feedstock stream on a solvent free basis.

Figure 8:
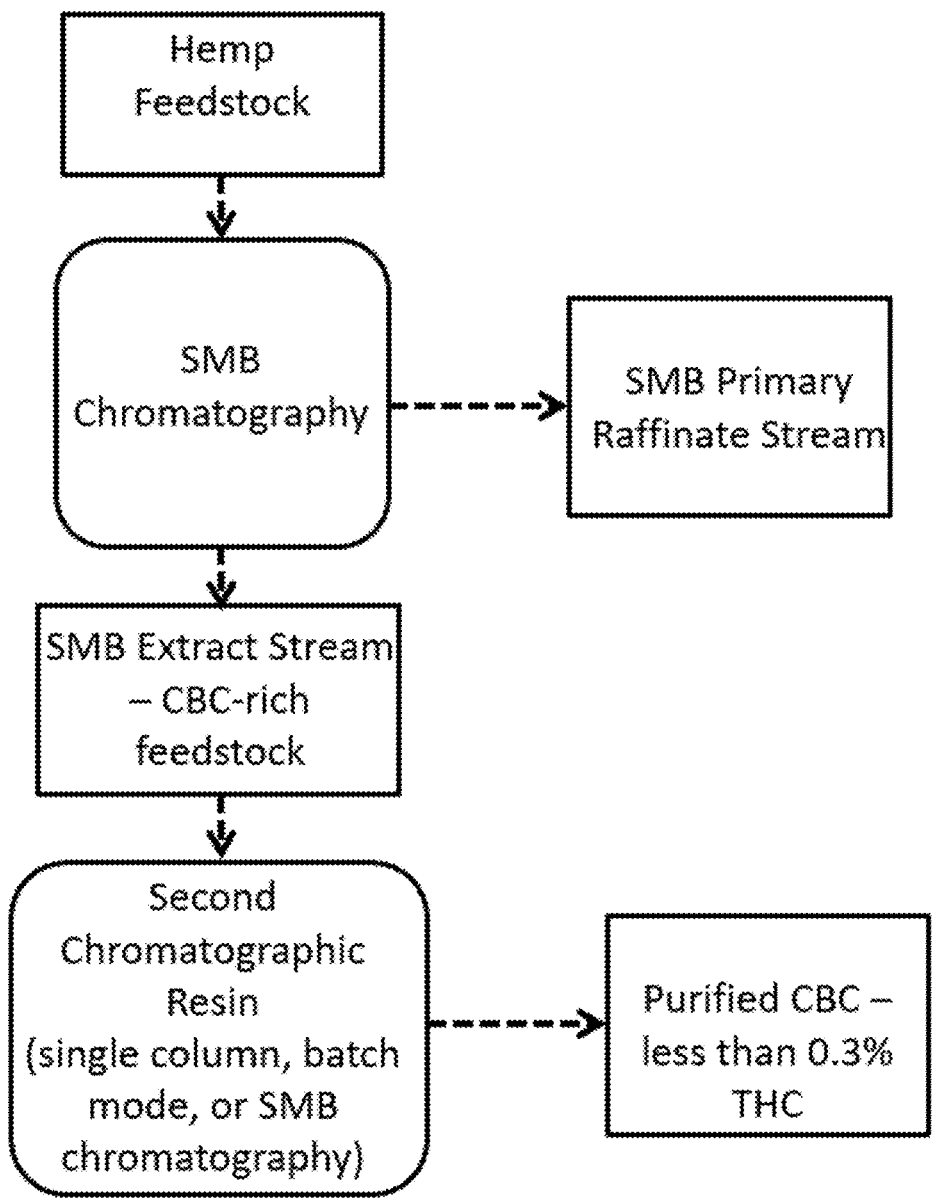
FIG. 8 is a schematic depicting the second illustrative aspect of the present disclosure.

In a second illustrative aspect of the disclosure, as depicted in FIG. 8, provided is a method of removing THC and/or THCA from a mixture, the mixture including THC and/or THCA and at least one cannabinoid (e.g., cannabichromene (CBC), cannabichromenic acid (CBCA), cannabinol (CBN), cannabigerol (CBG), cannabigerolic acid (CBGA), or a mixture thereof), the method comprising preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, the SMB extract stream having a higher weight percentage of THC and/or THCA on a solvent free basis and optionally a higher weight percentage of at least one cannabinoid than in the first feedstock stream on a solvent free basis; optionally removing at least a portion of the first solvent from the SMB extract stream to produce a concentrated SMB extract stream; preparing a second feedstock stream, the second feedstock stream comprising the SMB extract stream or the concentrated SMB extract stream and a second solvent; and passing the second feedstock stream through a second chromatographic resin to provide an eluate stream, the eluate stream having less than 0.3 wt % THC (e.g., less than 0.2 wt % or less than 0.1 wt %) on a solvent free basis and optionally a higher weight percentage of at least one cannabinoid than in the second feedstock stream on a solvent free basis.

In the second illustrative aspect of the disclosure, the at least one cannabinoid can be any suitable cannabinoid described herein (e.g., cannabichromene (CBC), cannabichromenic acid (CBCA), cannabinol (CBN), cannabigerol (CBG), cannabigerolic acid (CBGA), or a mixture thereof). However, in preferred embodiments of the second illustrative aspect of the disclosure, the at least one cannabinoid is cannabichromene (CBC).

Also in the second illustrative aspect of the disclosure, the first chromatographic resin and the second chromatographic resin are each independently selected from: (i) an activated carbon adsorbent, (ii) a silica adsorbent, (iii) a hydrophobic divinylbenzene-based adsorbent, (iv) an activated alumina adsorbent, (v) a reverse phase carbon-based adsorbent, and (vi) a combination thereof, as described herein. For example, the first chromatographic resin and the second chromatographic resin are each independently selected from (e.g., OR-1, OR-2, OR-2 prime, OR-3, OR-4, OR-5, OR-5 prime, and/or OR-11). In preferred embodiments of the second illustrative aspect of the disclosure, the first chromatographic resin is a hydrophobic divinylbenzene-based adsorbent (e.g., OR-5, OR-5 prime, and/or OR-11) and/or the second chromatographic resin is a silica adsorbent (e.g., OR-3).

In the second illustrative aspect of the disclosure, the first chromatographic resin arranged in a simulated moving bed (SMB) chromatography configuration and the second chromatographic resin can be disposed in a single column or more than one column in series. Thus the second chromatographic resin can be used in single column chromatography, batch column chromatography, or SMB chromatography. In a preferred embodiments of the second illustrative aspect of the disclosure, the second chromatographic resin is arranged in a simulated moving bed (SMB) chromatography configuration.

In the second illustrative aspect of the disclosure, the method can comprise regenerating the first chromatographic resin by washing the first chromatographic resin with a first regeneration solution to produce a first wash and/or regenerating the second chromatographic resin by washing the second chromatographic resin with a second regeneration solution to produce a second wash. In some embodiments, the solvent can be removed from the first wash and/or the second wash and the concentrated first wash or concentrated second wash can be used in subsequent steps in the process.

The second illustrative aspect of the disclosure utilizes the SMB extract stream of the first chromatographic resin arranged in a simulated moving bed (SMB) chromatography configuration as the second feedstock stream for the second chromatographic resin. Without wishing to be bound by any particular theory, it is believed that the second illustrative aspect allow what one would typically be consider a waste stream to be utilized in acquiring high purity cannabinoids such as cannabichromene (CBC). In some embodiments, the second illustrative aspect can be used to obtain an eluate stream having greater than 50 wt % CBC (e.g., greater than 60 wt % or greater than 70 wt %) and less than 0.3 wt % THC (e.g., less than 0.2 wt % or less than 0.1 wt %) on a solvent free basis.

Thus, in a preferred embodiment of the second illustrative aspect, disclosure provides a method of removing THC and/or THCA from a mixture, the mixture including THC and/or THCA and cannabichromene (CBC), the method comprising preparing a first feedstock stream from the mixture, the first feedstock stream comprising THC and/or THCA, cannabichromene (CBC), and a first solvent; passing the first feedstock stream through a hydrophobic divinylbenzene-based adsorbent arranged in a simulated moving bed (SMB) chromatography configuration to provide a primary raffinate stream and an SMB extract stream, the SMB extract stream having a higher weight percentage of THC and/or THCA on a solvent free basis and a higher weight percentage of cannabichromene (CBC) than in the first feedstock stream on a solvent free basis; optionally removing at least a portion of the first solvent from the SMB extract stream to produce a concentrated SMB extract stream; preparing a second feedstock stream, the second feedstock stream comprising the SMB extract stream or the concentrated SMB extract stream and a second solvent; and passing the second feedstock stream through a silica adsorbent to provide an eluate stream, the eluate stream having less than 0.3 wt % THC (e.g., less than 0.2 wt % or less than 0.1 wt %) on a solvent free basis and a higher weight percentage of cannabichromene (CBC) than in the second feedstock stream on a solvent free basis.

Other embodiments of the second illustrative aspect of the present disclosure will be readily apparent to one skilled in the art based upon the present disclosure provided herein, including the features of the first illustrative aspect of the present disclosure.

In a third illustrative aspect of the disclosure, the first and second illustrative aspects can be combined such that THC-free CBD and additional THC-free cannabinoids (e.g., cannabichromene (CBC), cannabichromenic acid (CBCA), cannabinol (CBN), cannabigerol (CBG), cannabigerolic acid (CBGA), or a mixture thereof) can be obtained concurrently using a single process.

Other embodiments of the third illustrative aspect of the present disclosure will be readily apparent to one skilled in the art based upon the present disclosure provided herein, including the features of the first and second illustrative aspects of the present disclosure.

In any of the aspects or embodiments described herein, passing the first feedstock stream through the first chromatographic resin arranged in a simulated moving bed (SMB) chromatography configuration can remove greater than 50 wt % (e.g., greater than 60 wt %, greater than 70 wt %, greater than 80 wt %, or greater than 90 wt %) of the THC from a mixture as measured by the mass of THC in the primary raffinate compared to the mass of THC in the mixture. For example, if the mixture used to prepare the first feedstock stream contains 3 grams of THC, passing the first feedstock stream through the first chromatographic resin arranged in a simulated moving bed (SMB) chromatography configuration can remove greater than 1.5 grams (e.g., greater than 1.8 grams, greater than 2.1 grams, greater than 2.4 grams, or greater than 2.7 grams) of THC. In other words, a simulated moving bed (SMB) chromatography configuration can be utilized to remove the bulk (i.e., majority) of THC from a mixture. Similarly, in any of the aspects or embodiments described herein, passing the second feedstock stream through the second chromatographic resin can remove up to 50 wt % (e.g., up to 40 wt %, up to 30 wt %, up to 20 wt %, or up to 10 wt %) of the THC from the mixture as measured by the mass of THC in the eluate stream compared to the mass of THC in the mixture. For example, if the mixture used to prepare the first feedstock stream, and consequently the second feedstock stream, contains 3 grams of THC, passing the second feedstock stream through the second chromatographic resin can remove up to 1.5 grams (e.g., up to 1.2 grams, up to 0.9 grams, up to 0.6 grams, or up to 0.3 grams) of THC. In other words, the second chromatographic resin can be utilized to remove the remainder of the THC after the bulk (i.e., majority) of THC has been removed from the mixture.

Thus, in a fourth illustrative aspect of the disclosure, the method includes preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, wherein passing the first feedstock stream through the first chromatographic resin arranged in a simulated moving bed (SMB) chromatography configuration removes greater than 50 wt % (e.g., greater than 60 wt %, greater than 70 wt %, greater than 80 wt %, or greater than 90 wt %) of the THC from the mixture as measured by the mass of THC in the primary raffinate compared to the mass of THC in the mixture; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent; and passing the second feedstock stream through a second chromatographic resin to provide an eluate stream, wherein passing the second feedstock stream through the second chromatographic resin removes up to 50 wt % (e.g., up to 40 wt %, up to 30 wt %, up to 20 wt %, or up to 10 wt %) of the THC from the mixture as measured by the mass of THC in the eluate stream compared to the mass of THC in the mixture.

Other embodiments of the fourth illustrative aspect of the present disclosure will be readily apparent to one skilled in the art based upon the present disclosure provided herein, including the features of the first, second, and third illustrative aspects of the present disclosure. In other embodiments of any one of the aspects of the present disclosure (e.g., the first, second, third, and fourth illustrative aspects of the disclosure), features of any of the other aspects of the present disclosure described herein can be used to further satisfy the principles of the present disclosure as will be appreciated by one skilled in the art.

Embodiments

Principles of the present disclosure are incorporated in the following embodiments:

Embodiment (1). A method of removing THC and/or THCA from a mixture, the mixture including THC and/or THCA and at least one cannabinoid, the method comprising: preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, the primary raffinate stream having less than 0.9 wt % THC on a solvent free basis and optionally a higher weight percentage of at least one cannabinoid than in the first feedstock stream on a solvent free basis; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent and the second feedstock stream having less than 0.9 wt % THC on a solvent free basis; and passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

Embodiment (2). The method of embodiment (1), wherein the at least one cannabinoid is cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof.

Embodiment (3). The method of embodiment (1) or embodiment (2), wherein the at least one cannabinoid is cannabidiol (CBD), cannabidiolic acid (CBDA), or a mixture thereof.

Embodiment (4). The method of any one of embodiments (1)-(3), wherein the mixture is a non-decolorized, non-decarboxylated hemp extract.

Embodiment (5). The method of any one of embodiments (1)-(3), wherein the mixture is a decolorized, non-decarboxylated hemp extract.

Embodiment (6). The method of any one of embodiments (1)-(3), wherein the mixture is a decolorized and decarboxylated hemp extract.

Embodiment (7). The method of any one of embodiments (1)-(6), wherein the primary raffinate stream and the second feedstock stream each have less than 0.8 wt % THC on a solvent free basis.

Embodiment (8). The method of any one of embodiments (1)-(7), wherein the primary raffinate stream and the second feedstock stream each have less than 0.75 wt % THC on a solvent free basis.

Embodiment (9). The method of any one of embodiments (1)-(8), wherein the first chromatographic resin and the second chromatographic resin are each independently selected from: (i) an activated carbon adsorbent, (ii) a silica adsorbent, (iii) a hydrophobic divinylbenzene-based adsorbent, (iv) an activated alumina adsorbent, (v) a reverse phase carbon-based adsorbent, and (vi) a combination thereof.

Embodiment (10). The method of any one of embodiments (1)-(9), wherein the first chromatographic resin is a hydrophobic divinylbenzene-based adsorbent.

Embodiment (11). The method of embodiment (10), wherein the hydrophobic divinylbenzene-based adsorbent has: (i) an average particle diameter of 20 microns to 600 microns, (ii) an average surface area of 450 $m^2/g$ to 900 $m^2/g$, (iii) an average pore size of 75 Å to 550 Å, (iv) an average water content of 35% to 80%, (v) an average bulk density of 0.45 g/mL to 0.9 g/mL, or (vi) any combination thereof.

Embodiment (12). The method of embodiment (10) or embodiment (11), wherein the hydrophobic divinylbenzene-based adsorbent is a polystyrene-divinylbenzene adsorbent.

Embodiment (13). The method of any one of embodiments (1)-(12), wherein the second chromatographic resin is an activated carbon adsorbent.

Embodiment (14). The method of embodiment (13), wherein the activated carbon adsorbent has: (i) an average particle diameter of 40 microns to 1700 microns, (ii) an iodine number of 900 mg/g or more, or (iii) a combination thereof.

Embodiment (15). The method of any one of embodiments (1)-(14), wherein the second chromatographic resin is disposed in a single column or more than one column in series.

Embodiment (16). The method of any one of embodiments (1)-(14), wherein the second chromatographic resin is arranged in a simulated moving bed (SMB) chromatography configuration.

Embodiment (17). The method of any one of embodiments (1)-(16), wherein the method further comprises: regenerating the first chromatographic resin by washing the first chromatographic resin with a first regeneration solution to produce a first wash and optionally concentrating the first wash.

Embodiment (18). The method of embodiment (17), wherein the first regeneration solution comprises ethanol, acetone, ethyl acetate, acetonitrile, pentanes, hexanes, heptanes, methanol, isopropyl alcohol, propanol, and a combination thereof.

Embodiment (19). The method of any one of embodiments (1)-(18), wherein the method further comprises: regenerating the second chromatographic resin by washing the second chromatographic resin with a second regeneration solution to produce a second wash and optionally concentrating the second wash.

Embodiment (20). The method of embodiment (19), wherein the second regeneration solution comprises ethanol, acetone, ethyl acetate, acetonitrile, pentanes, hexanes, heptanes, methanol, isopropyl alcohol, propanol, and a combination thereof.

Embodiment (21). The method of any one of embodiments (17)-(20), wherein the second feedstock stream further comprises the first wash or the concentrated first wash.

Embodiment (22). The method of any one of embodiments (1)-(21), wherein the first solvent is selected from water, ethanol, acetone, ethyl acetate, acetonitrile, pentanes, hexanes, heptanes, methanol, isopropyl alcohol, propanol, and a combination thereof.

Embodiment (23). The method of any one of embodiments (1)-(22), wherein the second solvent is selected from water, ethanol, acetone, ethyl acetate, acetonitrile, pentanes, hexanes, heptanes, methanol, isopropyl alcohol, propanol, and a combination thereof.

Embodiment (24). The method of any one of embodiments (1)-(23), the eluate stream having a trace amount of THC on a solvent free basis.

Embodiment (25). The method of any one of embodiments (1)-(24), the eluate stream having no detectable amount of THC on a solvent free basis.

Embodiment (26). A method of removing THC and/or THCA from a mixture, the mixture including THC and/or THCA and at least one cannabinoid, the method comprising: preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, the SMB extract stream having a higher weight percentage of THC and/or THCA on a solvent free basis and optionally a higher weight percentage of at least one cannabinoid than in the first feedstock stream on a solvent free basis; optionally removing at least a portion of the first solvent from the SMB extract stream to produce a concentrated SMB extract stream; preparing a second feedstock stream, the second feedstock stream comprising the SMB extract stream or the concentrated SMB extract stream and a second solvent; and passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

Embodiment (27). The method of embodiment (26), wherein the at least one cannabinoid is cannabichromene (CBC), cannabichromenic acid (CBCA), cannabinol (CBN), cannabigerol (CBG), cannabigerolic acid (CBGA), or a mixture thereof.

Embodiment (28). The method of embodiment (26) or embodiment (27), wherein the at least one cannabinoid comprises cannabichromene (CBC).

Embodiment (29). The method of any one of embodiments (26)-(28), wherein the mixture is a non-decolorized, non-decarboxylated hemp extract.

Embodiment (30). The method of any one of embodiments (26)-(28), wherein the mixture is a decolorized, non-decarboxylated hemp extract.

Embodiment (31). The method of any one of embodiments (26)-(28), wherein the mixture is a decolorized and decarboxylated hemp extract.

Embodiment (32). The method of any one of embodiments (26)-(31), wherein the first chromatographic resin and the second chromatographic resin are each independently selected from: (i) an activated carbon adsorbent, (ii) a silica adsorbent, (iii) a hydrophobic divinylbenzene-based adsorbent, (iv) an activated alumina adsorbent, (v) a reverse phase carbon-based adsorbent, and (vi) a combination thereof.

Embodiment (33). The method of any one of embodiments (26)-(32), wherein the first chromatographic resin is a hydrophobic divinylbenzene-based adsorbent.

Embodiment (34). The method of embodiment (33), wherein the hydrophobic divinylbenzene-based adsorbent has: (i) an average particle diameter of 20 microns to 600 microns, (ii) an average surface area of 450 $m^2$/g to 900 $m^2$/g, (iii) an average pore size of 75 Å to 550 Å, (iv) an average water content of 35% to 80%, (v) an average bulk density of 0.45 g/mL to 0.9 g/mL, or (vi) any combination thereof.

Embodiment (35). The method of embodiment (33) or embodiment (34), wherein the hydrophobic divinylbenzene-based adsorbent is a polystyrene-divinylbenzene adsorbent.

Embodiment (36). The method of any one of embodiments (26)-(35), wherein the second chromatographic resin is a silica adsorbent.

Embodiment (37). The method of embodiment (36), wherein the silica adsorbent has: (i) an average particle diameter of 25 microns to 300 microns, (ii) an average surface area of 350 $m^2$/g to 850 $m^2$/g, (iii) an average pore size of 40 Å to 1000 Å, (iv) an average bulk density of 0.4 g/mL to 0.8 g/mL, (v) an average pore volume of 0.7 mL/g to 0.85 mL/g, or (vi) any combination thereof.

Embodiment (38). The method of any one of embodiments (26)-(37), wherein the second chromatographic resin is disposed in a single column or more than one column arranged in series.

Embodiment (39). The method of any one of embodiments (26)-(37), wherein the second chromatographic resin is arranged in a simulated moving bed (SMB) chromatography configuration.

Embodiment (40). The method of any one of embodiments (26)-(39), wherein the method further comprises: regenerating the first chromatographic resin by washing the first chromatographic resin with a first regeneration solution to produce a first wash and optionally concentrating the first wash.

Embodiment (41). The method of embodiment (40), wherein the first regeneration solution comprises ethanol, acetone, ethyl acetate, acetonitrile, pentanes, hexanes, heptanes, methanol, isopropyl alcohol, propanol, and a combination thereof.

Embodiment (42). The method of any one of embodiments (26)-(41), wherein the method further comprises: regenerating the second chromatographic resin by washing the second chromatographic resin with a second regeneration solution to produce a second wash and optionally concentrating the second wash.

Embodiment (43). The method of embodiment (42), wherein the second regeneration solution comprises ethanol, acetone, ethyl acetate, acetonitrile, pentanes, hexanes, heptanes, methanol, isopropyl alcohol, propanol, and a combination thereof.

Embodiment (44). The method of any one of embodiments (40)-(43), wherein the second feedstock stream further comprises the first wash or the concentrated first wash.

Embodiment (45). The method of any one of embodiments (26)-(44), wherein the first solvent is selected from water, ethanol, acetone, ethyl acetate, acetonitrile, pentanes, hexanes, heptanes, methanol, isopropyl alcohol, propanol, and a combination thereof.

Embodiment (46). The method of any one of embodiments (26)-(45), wherein the second solvent is selected from water, ethanol, acetone, ethyl acetate, acetonitrile, pentanes, hexanes, heptanes, methanol, isopropyl alcohol, propanol, and a combination thereof.

Embodiment (47). The method of any one of embodiments (28)-(46), the eluate stream having greater than 50 wt % CBC on a solvent free basis.

Embodiment (48). The method of any one of embodiments (28)-(47), the eluate stream having greater than 60 wt % CBC on a solvent free basis.

Embodiment (49). A method of removing THC and/or THCA from a mixture, the mixture including THC and/or THCA and at least one cannabinoid, the method comprising: preparing a first feedstock stream from the mixture, the first feedstock stream comprising THC and/or THCA, at least one cannabinoid, and a first solvent; passing the first feedstock stream through a first chromatographic resin arranged in a simulated moving bed (SMB) chromatography configuration to provide a primary raffinate stream and an SMB extract stream, wherein passing the first feedstock stream through the first chromatographic resin arranged in a simulated moving bed (SMB) chromatography configuration removes greater than 50 wt % of the THC from the mixture as measured by the mass of THC in the primary raffinate compared to the mass of THC in the mixture; optionally removing at least a portion of the first solvent from the primary raffinate stream to produce a concentrated primary raffinate stream; preparing a second feedstock stream, the second feedstock stream comprising the primary raffinate stream or the concentrated primary raffinate stream and a second solvent; and passing the second feedstock stream through a second chromatographic resin to provide an eluate stream, wherein passing the second feedstock stream through the second chromatographic resin removes up to 50 wt % of the THC from the mixture as measured by the mass of THC in the eluate stream compared to the mass of THC in the mixture.

Embodiment (50). The method of embodiment (49), wherein the at least one cannabinoid is cannabidiol (CBD), cannabidiolic acid (CBDA), cannabichromene (CBC), cannabichromenic acid (CBCA), cannabinol (CBN), cannabigerol (CBG), cannabigerolic acid (CBGA), or a mixture thereof.

Embodiment (51). The method of embodiment (49) or embodiment (50), wherein the at least one cannabinoid is cannabidiol (CBD), cannabidiolic acid (CBDA), or a mixture thereof.

Embodiment (52). The method of any one of embodiments (49)-(51), wherein the mixture is a non-decorloized, non-decarboxylated hemp extract.

Embodiment (53). The method of any one of embodiments (49)-(51), wherein the mixture is a decolorized, non-decarboxylated hemp extract.

Embodiment (54). The method of any one of embodiments (49)-(51), wherein the mixture is a decolorized and decarboxylated hemp extract.

Embodiment (55). The method of any one of embodiments (49)-(54), wherein passing the first feedstock stream through the first chromatographic resin arranged in a simulated moving bed (SMB) chromatography configuration removes greater than 60 wt % of the THC from the mixture as measured by the mass of THC in the primary raffinate compared to the mass of THC in the mixture, and wherein passing the second feedstock stream through the second chromatographic resin removes up to 40 wt % of the THC from the mixture as measured by the mass of THC in the eluate stream compared to the mass of THC in the mixture.

Embodiment (56). The method of any one of embodiments (49)-(55), wherein passing the first feedstock stream through the first chromatographic resin arranged in a simulated moving bed (SMB) chromatography configuration removes greater than 70 wt % of the THC from the mixture as measured by the mass of THC in the primary raffinate compared to the mass of THC in the mixture, and wherein passing the second feedstock stream through the second chromatographic resin removes up to 30 wt % of the THC from the mixture as measured by the mass of THC in the eluate stream compared to the mass of THC in the mixture.

Embodiment (57). The method of any one of embodiments (49)-(56), wherein the first chromatographic resin and the second chromatographic resin are each independently selected from:
(i) an activated carbon adsorbent,
(ii) a silica adsorbent,
(iii) a hydrophobic divinylbenzene-based adsorbent,
(iv) an activated alumina adsorbent,
(v) a reverse phase carbon-based adsorbent, and
(vi) a combination thereof.

Embodiment (58). The method of any one of embodiments (49)-(57), wherein the first chromatographic resin is a hydrophobic divinylbenzene-based adsorbent.

Embodiment (59). The method of embodiment (58), wherein the hydrophobic divinylbenzene-based adsorbent has:
(i) an average particle diameter of 20 microns to 600 microns,
(ii) an average surface area of 450 $m^2/g$ to 900 $m^2/g$,
(iii) an average pore size of 75 Å to 550 Å,
(iv) an average water content of 35% to 80%,
(v) an average bulk density of 0.45 g/mL to 0.9 g/mL, or
(vi) any combination thereof.

Embodiment (60). The method of embodiment (58) or embodiment (59), wherein the hydrophobic divinylbenzene-based adsorbent is a polystyrene-divinylbenzene adsorbent.

Embodiment (61). The method of any one of embodiments (49)-(60), wherein the second chromatographic resin is an activated carbon adsorbent.

Embodiment (62). The method of embodiment (61), wherein the activated carbon adsorbent has:
(i) an average particle diameter of 40 microns to 1700 microns,
(ii) an iodine number of 900 mg/g or more, or
(iii) a combination thereof.

Embodiment (63). The method of any one of embodiments (49)-(62), wherein the second chromatographic resin is disposed in a single column or more than one column in series.

Embodiment (64). The method of any one of embodiments (49)-(62), wherein the second chromatographic resin is arranged in a simulated moving bed (SMB) chromatography configuration.

Embodiment (65). The method of any one of embodiments (49)-(64), wherein the method further comprises: regenerating the first chromatographic resin by washing the first chromatographic resin with a first regeneration solution to produce a first wash and optionally concentrating the first wash.

Embodiment (66). The method of embodiment (65), wherein the first regeneration solution comprises ethanol, acetone, ethyl acetate, acetonitrile, pentanes, hexanes, heptanes, methanol, isopropyl alcohol, propanol, and a combination thereof.

Embodiment (67). The method of any one of embodiments (49)-(66), wherein the method further comprises:

regenerating the second chromatographic resin by washing the second chromatographic resin with a second regeneration solution to produce a second wash and optionally concentrating the second wash.

Embodiment (68). The method of embodiment (67), wherein the second regeneration solution comprises ethanol, acetone, ethyl acetate, acetonitrile, pentanes, hexanes, heptanes, methanol, isopropyl alcohol, propanol, and a combination thereof.

Embodiment (69). The method of any one of embodiments (65)-(68), wherein the second feedstock stream further comprises the first wash or the concentrated first wash.

Embodiment (70). The method of any one of embodiments (49)-(69), wherein the first solvent is selected from water, ethanol, acetone, ethyl acetate, acetonitrile, pentanes, hexanes, heptanes, methanol, isopropyl alcohol, propanol, and a combination thereof.

Embodiment (71). The method of any one of embodiments (49)-(70), wherein the second solvent is selected from water, ethanol, acetone, ethyl acetate, acetonitrile, pentanes, hexanes, heptanes, methanol, isopropyl alcohol, propanol, and a combination thereof.

Embodiment (72). The method of any one of embodiments (49)-(71), the eluate stream having less than 0.3 wt % THC on a solvent free basis.

Embodiment (73). The method of any one of embodiments (49)-(72), the eluate stream having a trace amount of THC on a solvent free basis.

Embodiment (74). The method of any one of embodiments (49)-(73), the eluate stream having no detectable amount of THC on a solvent free basis.

The foregoing exemplary embodiments of the disclosure numbered 1-74 are non-limiting. Other exemplary embodiments are apparent from the entirety of the description herein. As will be apparent to those of skill in the art upon reading this disclosure, each of the individually numbered embodiments may be used or combined with any of the preceding or following individually numbered embodiments.

EXAMPLES

The following examples are provided to illustrate the present disclosure. These examples are shown for illustrative purposes, and any disclosures embodied therein should not be limited thereto.

Example 1—Extraction of *Cannabis* Leaves with Ethanol

Figure 2:
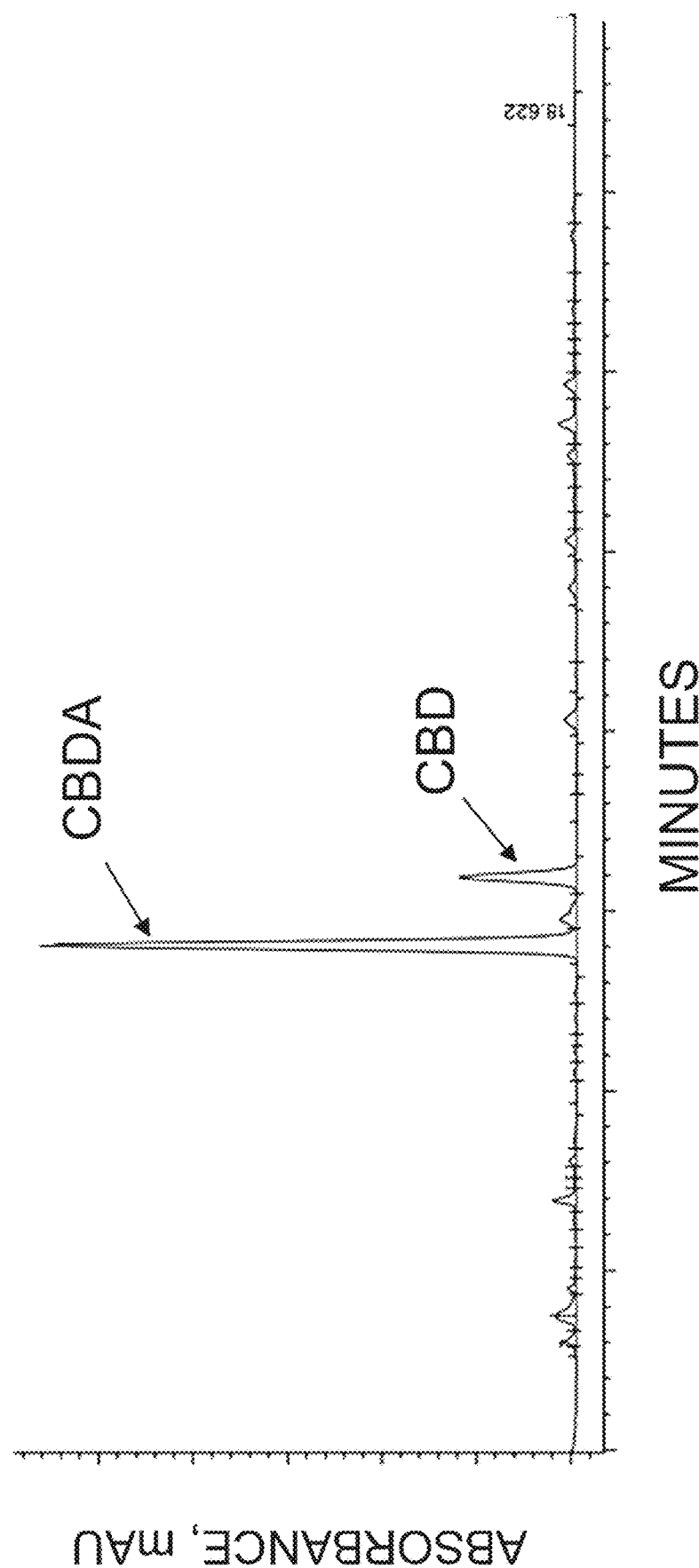
FIG. 2 is a High Performance Liquid Chromatography (HPLC) chromatographic area plot showing the results of a composition analysis of cannabinoids in the extract of dried hemp leaves.
Figure 5:
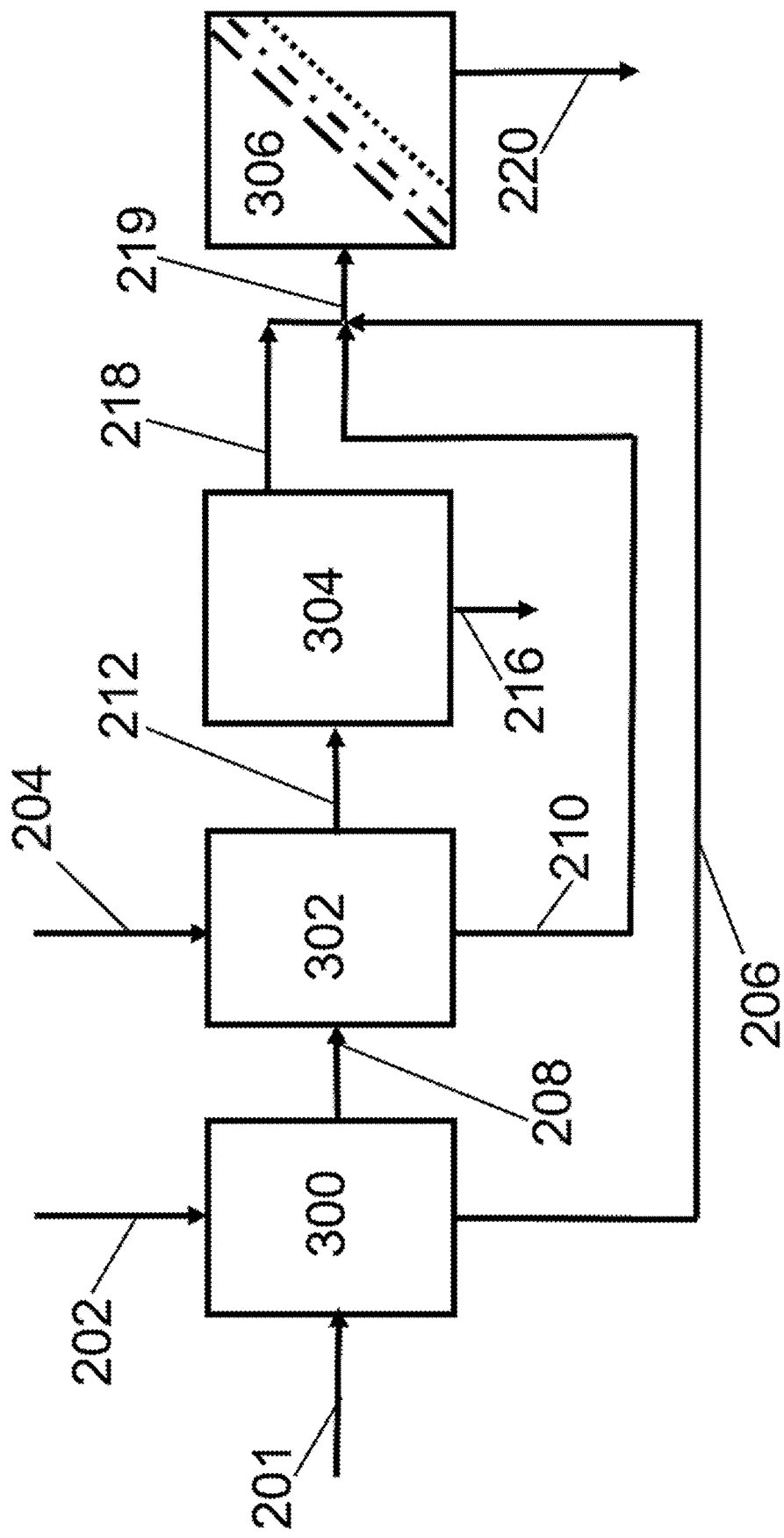
FIG. 5 is a schematic process flow diagram of the leaf extraction and filtration steps in one embodiment of the disclosure.

FIG. 5 is a schematic process flow diagram of the leaf extraction and filtration steps of embodiments of the disclosure. With reference to FIG. 5, about 150 Kg of dried cannabis leaves, shown in 201, was added to a 1000 Liter tote 300 and about 600 Liters of food grade ethanol (200 proof) was introduced to the tote 300 via line 202 to create a leaf/solvent mixture. The leaf/solvent mixture was agitated using a pneumatic mixer for a period of two hours at room temperature of about 25° C. at atmospheric pressure and allowed to stand overnight for an effective time (about 8 to 12 hours) to form a first ethanol layer. The first ethanol layer over the wet leaves was removed as a first decant stream in line 206. Shown as a second extraction step in tote 302, which may physically be the same as tote 300. A second portion of ethanol comprising 400 Liters of food grade ethanol was introduced via line 204 and again the leaf/solvent mixture was agitated in a second mixing step using a pneumatic mixer for a period of two hours at room temperature of about 25° C. at atmospheric pressure in a second extraction step. At the conclusion of the second mixing step, a second decant stream in line 210 was withdrawn and the remaining wet leaves were passed to a screw type extraction press (VINCENT Model CP10 available from Vincent Corporation, Tampa, Florida) wherein the solids were pressed or squeezed, resulting in a third liquid decant stream in line 218 and used or spent leaves. The used or spend leaves shown as stream 216 are withdrawn and passed to waste disposal. The first, second and third decant streams (206, 210 and 218) were combined and passed to a filtration zone 306 as a liquid leaf extract stream in line 219. Following extraction the solid concentration of the liquid leaf extract stream comprised of 35-40% cannabidiol and cannabidiolic acid. The solid/oil concentration of total solids/oils (as measured following evaporation of the solvent from the liquid leaf extract stream) in the liquid leaf extract stream was approximately 25-30 g/L. The liquid leaf extract stream or crude cannabis extract stream was decanted and filtered in the filtration zone 306 to remove solid particles, by passing the liquid leaf extract stream through three successive filters of decreasing pore size: 100 micron, 20 micron, and 10 micron. The 100 micron pore size filter comprised a bag made of felt for high capacity flow and capturing solids. The 20 and 10 micron pore size filters were cartridges comprising polyethylene and were pleated for higher surface area. The cartridges had O-rings on a fitting at the end for seating inside a stainless steel cylindrical housing. The filtered liquid leaf extract stream was green in color, was essentially free of particles, and comprised approximately 20-40 g/L of cannabidiol (CBD) and cannabidiolic acid (CBDA). FIG. 2 illustrates a High Performance Liquid Chromatography (HPLC) chromatographic area plot showing the results of a composition analysis of cannabinoids in the filtered liquid extract stream. Table 1 shows the composition of the filtered liquid extract stream or filtered crude cannabinoid stream from the extract of industrial hemp leaves.

TABLE 1

| Extracted Material from Industrial Hemp Leaves | |
|---|---|
| Compound | Amount Reported, wt % |
| THC | 0.1 |
| THCV | 0.0 |
| CBG | 1.0 |
| CBD | 4.0 |
| CBN | 1.0 |
| THCA | 1.8 |
| CBDA | 25.0 |
| CBDV | 0.0 |
| Other | 67.1 |
| Total | 100.0 |

Example 2—Removal of Chlorophylls and Other Impurities

Figure 3:
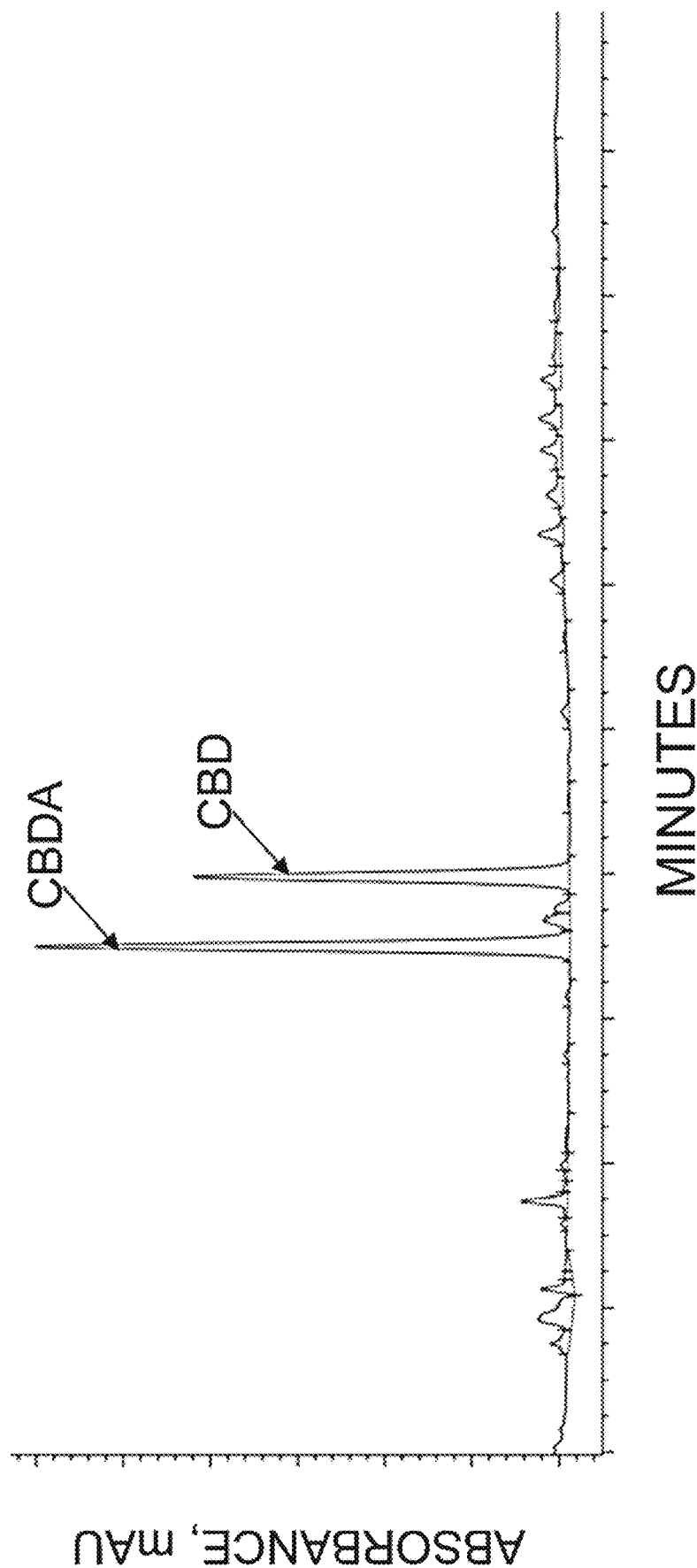
FIG. 3 is a High Performance Liquid Chromatography (HPLC) chromatographic area plot showing the results of a composition analysis of the cannabinoids in decolorized extract.

The green, filtered liquid extract stream, or filtered crude cannabinoid stream of Example 1 was loaded into a column chromatography zone to remove chlorophylls and other impurities. The filtered liquid leaf extract stream was passed through a 10 um filter to the top of a decolorization chromatographic column. The decolorization chromatographic column was comprised of polypropylene, having an inside diameter of 60 cm and a length of 183 cm (24 inches by 72 inches) and having an internal volume of 450 L (119 gal). The column was operated at a decolorization pressure of 2.72 atm to about 4.08 atm (40-60 psig) and a decolorization temperature ranging from 20-25° C. The flow rate used for the decolorization chromatographic column was between 2-3 L/min. The decolorization chromatographic column was packed with OR1 adsorbent. OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. Essentially all chlorophylls were removed from the filtered liquid extract stream, and the resulting concentration of the solids/oils in the extract stream was about 40-45% cannabidiol (CBD) and cannabidiolic acid (CBDA) and the concentration of total solids/oils in the stream was approximately 20-35 g/L concentration. An HPLC trace of cannabinoids present within decolorized hemp leaf extract, or decolorized crude extract stream is shown in FIG. 3. In FIG. 3, the cannabidiol (CBD) and cannabidiolic acid (CBDA) composition peaks are essentially unchanged from FIG. 2. Thus, no chemical change occurred during the decolorization process, however the color observed in the resulting decolorized extract stream changed from green to amber. Table 2 shows the composition of the decolorized extract stream.

TABLE 2

Composition of Decolorized Extract Stream

| Compound | Amount Reported, wt % |
|---|---|
| THC | 0.11 |
| THCV | 0.0 |
| CBG | 1.1 |
| CBD | 4.4 |
| CBN | 1.1 |
| THCA | 1.98 |
| CBDA | 35.0 |
| CBDV | 0.0 |
| Other | 63.81 |
| Total | 100.00 |

Example 3—Activation or Conversion of CBDA into CBD and THCA into THC

Figure 4:
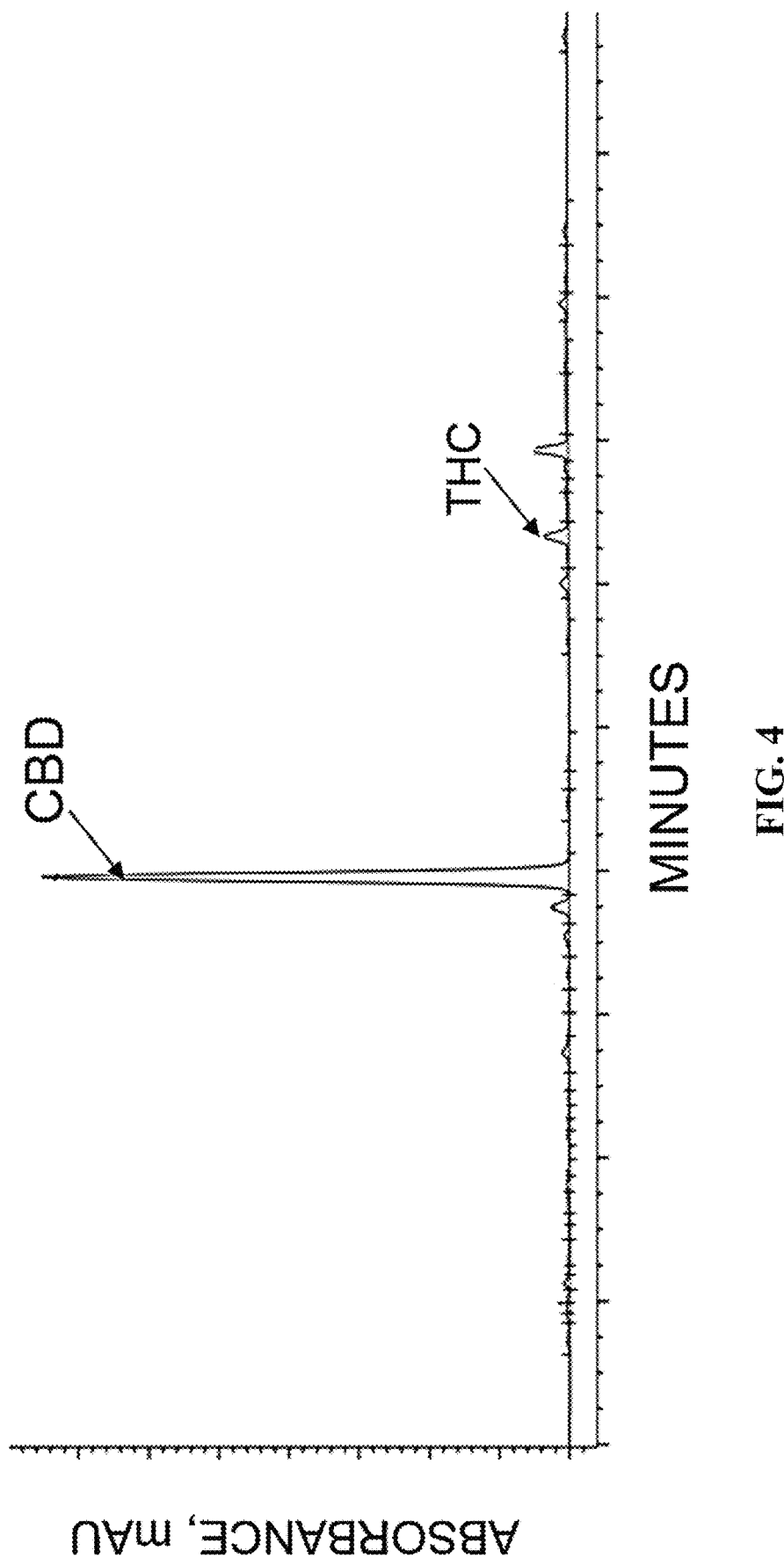
FIG. 4 is a High Performance Liquid Chromatography (HPLC) chromatographic area plot showing the results of a composition analysis of cannabinoids in activated extract.

The decolorized hemp leaf extract stream prepared in Example 2 was passed to a vacuum distillation unit, to remove essentially all of the solvent from the mixture. The vacuum distillation condenser had a 240 L capacity. This unit was operated at a vacuum pressure of −0.602 to −0.735 atm (−18 to −22 in Hg) and a temperature of 90-110° C. At least a portion of ethanol solvent recovered from the vacuum distillation unit was reused as solvent for the hemp leaf extraction step, described in Example 1. Following removal of the solvent, the resulting oil was retained in the vacuum distillation vessel at a decarboxylation temperature of 90 to 120° C. and a decarboxylation pressure of about −0.6 to 0.74 atm for an additional 5 to 8 hours, to permit sufficient time for the decarboxylation reaction to occur. The decarboxylation reaction time was sufficient to fully decarboxylate essentially all of the acidic components to provide a decarboxylated hemp oil. During the course of the decarboxylation reaction it was observed that some of the impurities in the feed were aggregated into a sludge like material which floated on top of the decarboxylated hemp oil. The aggregated impurities were removed, by subjecting the decarboxylated hemp oil to a water wash step to solubilize the impurities and remove the impurities from the decarboxylated hemp oil. FIG. 4 is an HPLC trace of cannabinoids present within decarboxylated hemp oil. In FIG. 4 a CBD peak was observed, but there was no CBDA peak present. The absence of a CBDA peak showed that the decarboxylation reaction of CBDA to CBD has proceeded to completion. The THC peak appears more prominently in FIG. 4 than before, which indicates that any THCA, although present in very small amounts in the decarboxylated hemp oil, has also been converted to THC. Table 3 shows the composition of the activated or decarboxylated cannabinoid oil stream.

TABLE 3

Composition of Decarboxylated Cannabinoid Oil

| Compound | Amount Reported, wt % |
|---|---|
| THC | 2.09 |
| THCV | 0.0 |
| CBG | 1.1 |
| CBD | 40.0 |
| CBN | 1.1 |
| THCA | 0.0 |
| CBDA | 0.0 |
| CBDV | 0.0 |
| Other | 55.41 |
| Total | 100.00 |

Example 4—OR-5 SMB Technology for THC and THCA Removal

The decolorized hemp extract of Example 2 can be used as feed to purify CBDA and CBD, and to remove THCA & THC, using SMB technology with OR-5 as the adsorbent. In the pilot scale run, 8.8 mg of decolorized extract was dissolved for every mL of solvent (95/5 v/v Ethanol/Heptane, from Pharmco-Aaper). Eight columns, each measuring 6 in. in diameter and 36 in. in length, were connected to the Simulated Moving Bed instrument (from Semba Bioscience—WI, USA). Four pumps (0-2.5 L/min) were also connected to the SMB Instrument. The SMB Step time was set at 1320 seconds and the system was maintained at 25° C. The flow rates for the above-mentioned streams are tabulated in Table 4, while the mass distribution percent of each bulk stream is given in Table 5.

TABLE 4

Flow Rates for the Zones in SMB of Example 4

| | Flow rate (L/min) |
|---|---|
| Desorbent (Zone 1 In) | 1.5 |
| Feed | 0.8 |
| Extract In (Zone 2 In) | 0.8 |
| Intermediate Flow (Zone 3 In) | 0.8 |
| Primary Raffinate (Zone 3 Out) | 0.88 |
| Secondary Raffinate (Zone 4 Out) | 0.6 |

TABLE 5

Mass Percent in Each Bulk Stream in SMB of Example 4

| SMB Outputs | Mass Distribution (%) | | | |
|---|---|---|---|---|
| | CBDA | CBD | THCA | THC |
| Extract | 4.64 | 25.93 | 42.92 | 99.28 |
| Primary Raffinate | 95.09 | 74.07 | 53.18 | 0 |
| Secondary Raffinate | 0.26 | 0 | 3.9 | 0.72 |

As is apparent from the results set forth in Table 5, the majority of the CBDA and CBD was present in the primary raffinate, whereas the majority of the THC was found in the extract stream.

Example 5—OR-5 SMB Technology for THC Removal

The decolorized and decarboxylated hemp extract of Example 3 can be used as feed to purify CBD and to remove THC using SMB technology with OR-5 as the adsorbent. In the pilot scale run, 64.1 mg of decolorized and decarboxylated extract was dissolved for every mL of solvent (95/5 v/v Ethanol/Heptane, from Pharmco-Aaper). Eight columns, measuring 6 in. in diameter and 36 in. in length, were connected to the Simulated Moving Bed instrument (from Semba Bioscience—WI, USA). Four pumps (0-2.5 L/min from Tuthill) were also connected to the SMB Instrument. The columns were figured to run in a 2-3-2-1 scheme. The SMB Step time was set at 1210 seconds and the system was maintained at 25° C. The flow rates for the above-mentioned streams are tabulated in Table 6, while the mass distribution percent of each bulk stream is given in Table 7.

TABLE 6

Flow Rates for the Zones in SMB of Example 5

| | Flow rate (L/min) |
|---|---|
| Desorbent (Zone 1 In) | 1.2 |
| Feed | 0.41 |
| Extract In (Zone 2 In) | 1.05 |
| Intermediate Flow (Zone 3 In) | 1.05 |
| Primary Raffinate (Zone 3 Out) | 0.53 |
| Secondary Raffinate (Zone 4 Out) | 0.9 |

TABLE 7

Mass Percent in Each Bulk Stream in SMB of Example 5

| SMB Outputs | Mass Distribution (%) | |
|---|---|---|
| | CBD | THC |
| Extract | 2.88 | 23.60 |
| Primary Raffinate | 84.69 | 43.15 |
| Secondary Raffinate | 12.42 | 33.25 |

As is apparent from the results set forth in Table 7, the majority of the CBD was present in the primary raffinate.

Example 6—Batch Chromatography after SMB Chromatography

This example demonstrates the benefit of performing bulk THC removal with SMB chromatography prior to trace THC removal with batch chromatography.

Figure 9:
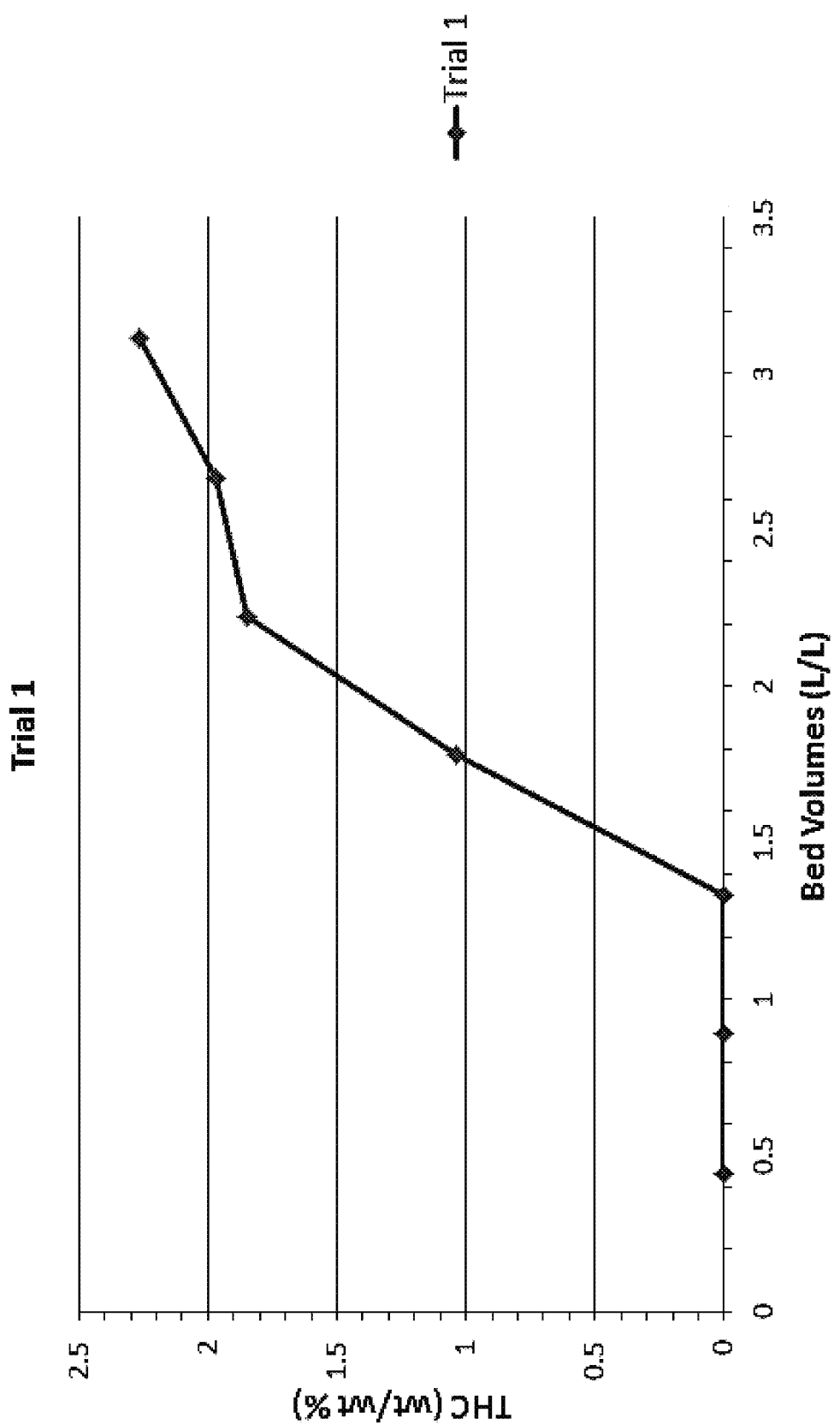
FIG. 9 is a graph showing the amount of THC (wt/wt %) vs. bed volume (L/L) for Trial 1, i.e., a mixture processed by OR-1 using batch chromatography, as described in Example 6.

The decolorized and decarboxylated hemp extract of Example 3, containing approximately 2.03 wt % THC, was used as feed to purify CBD by removal of THC along with polar lipids and waxes using OR-1 adsorbent in a batch chromatographic mode. In the Trial 1 pilot scale run, 15-30 mg of hemp extract was dissolved for every mL of solvent (95/5 v/v Ethanol/Heptane, from Pharmco-Aaper). The column, measuring 18 in. in diameter and 48 in. in length, was connected to a single pump (0-2.5 L/min from Tuthill). The flow rate was set to 0.5 L per minute and the system was maintained at 25° C. The graph of Trial 1 in FIG. 9 shows a plot of THC accumulation (wt/wt %) versus bed volume (L/L) of feed processed. As demonstrated by Trial 1 shown in FIG. 9, when using OR-1 adsorbent in a batch chromatographic mode to purify a mixture having approximately 2.03 wt % THC, only approximately 1.5 bed volumes (L/L) are created before THC starts accumulating.

Figure 10:
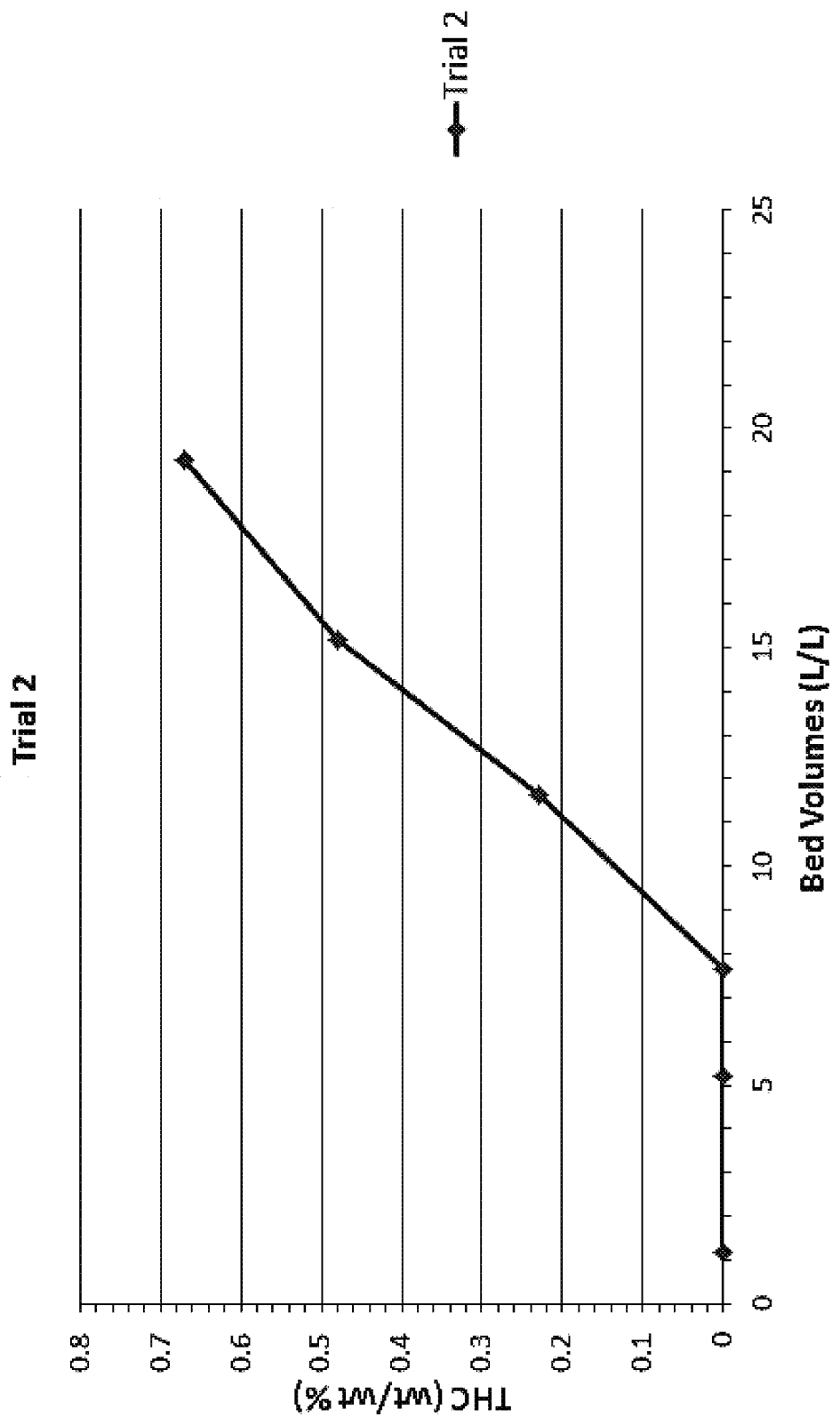
FIG. 10 is a graph showing the amount of THC (wt/wt %) vs. bed volume (L/L) for Trial 2, i.e., a mixture processed by OR-1 using batch chromatography after SMB chromatography with OR-5, as described in Example 6.

In contrast, SMB technology primary raffinate as described in Example 5, containing approximately 0.6 wt % THC, was used as feed to purify CBD by removal of THC using OR-1 adsorbent in a batch chromatographic mode. In the Trial 2 pilot scale run, 15-30 mg of hemp extract was dissolved for every mL of solvent (95/5 v/v Ethanol/Heptane, from Pharmco-Aaper). The column, measuring 18 in. in diameter and 48 in. in length, was connected to a single pump (0-2.5 L/min from Tuthill). The flow rate was set to 0.5 L per minute and the system was maintained at 25° C. The graph of Trial 2 in FIG. 10 shows a plot of THC accumulation (wt/wt %) versus bed volume (L/L) of feed processed. As demonstrated by Trial 2 shown in FIG. 10, when using OR-1 adsorbent in a batch chromatographic mode to purify a mixture having approximately 0.6 wt % THC, obtained by SMB chromatography, approximately 7.7 bed volumes (L/L) are created before THC starts accumulating. Thus, the number of THC free bed volumes are increased significantly by performing bulk THC removal with SMB chromatography prior to trace THC removal with batch chromatography.

Figure 11:
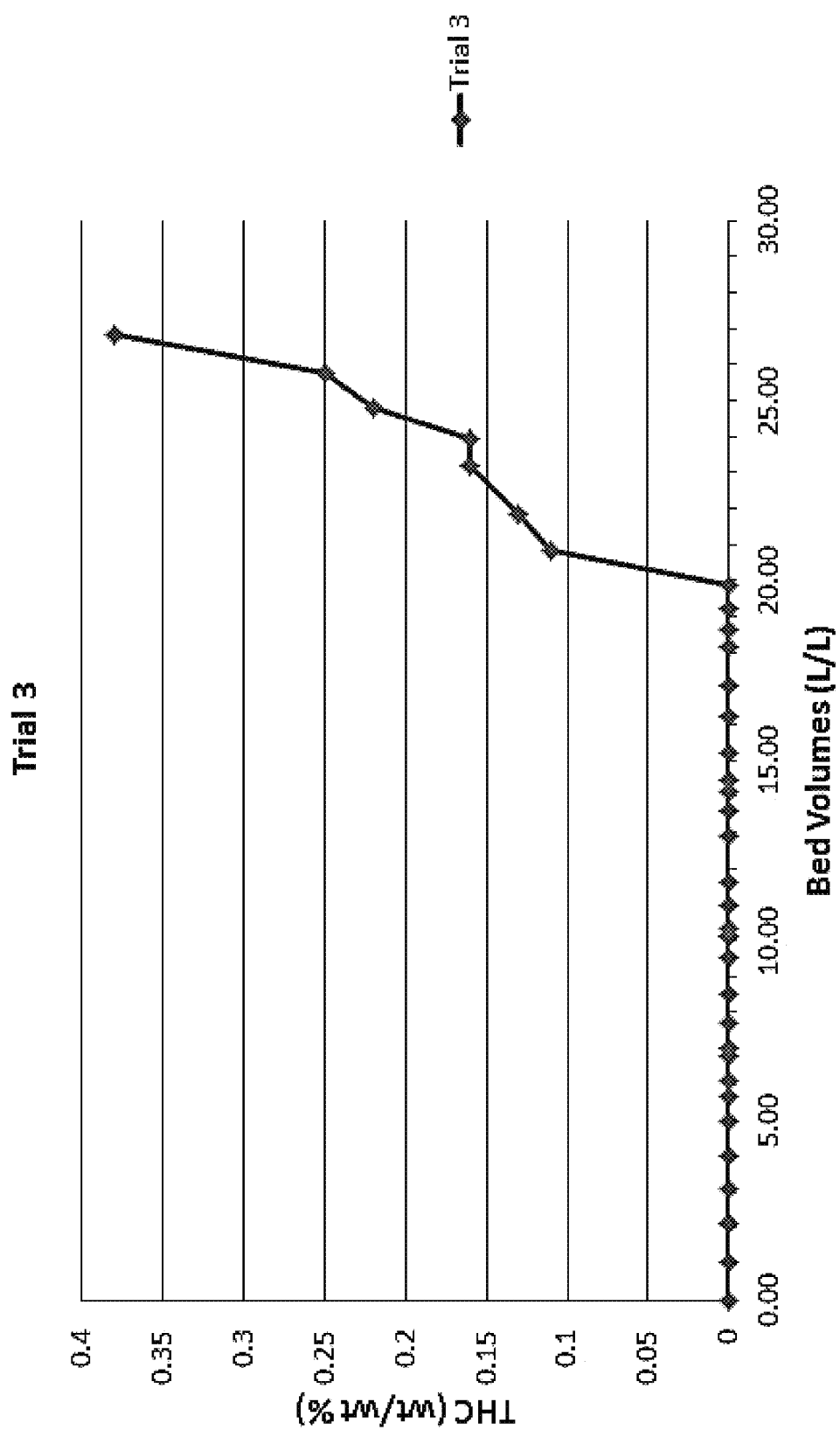
FIG. 11 is a graph showing the amount of THC (wt/wt %) vs. bed volume (L/L) for Trial 3, i.e., a mixture processed by OR-1 using batch chromatography after SMB chromatography with OR-5, as described in Example 6.

If the SMB technology primary raffinate is reduced to approximately 0.35 wt % THC, purifying CBD by removal of THC using OR-1 adsorbent in a batch chromatographic mode can produce as many as 20 THC free bed volumes (L/L), as demonstrated by the THC accumulation chart presented for Trial 3 in FIG. 11, which used SMB technology primary raffinate, containing approximately 0.35 wt % THC, as feed.

Figure 12:
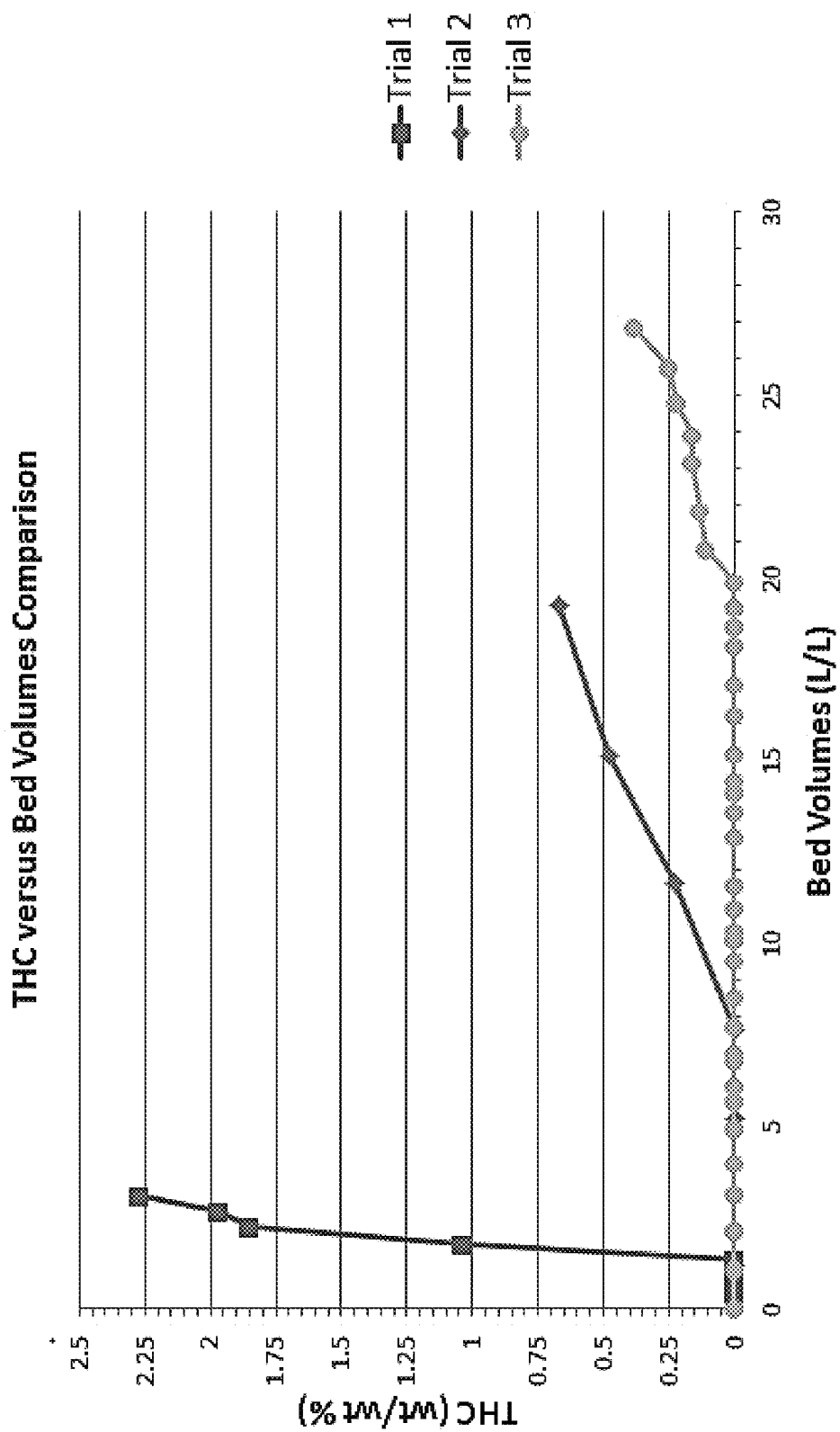
FIG. 12 is an overlay graph showing the amount of THC (wt/wt %) vs. bed volume (L/L) for Trials 1-3, i.e., a mixture processed by OR-1 using batch chromatography vs. being processed by OR-1 using batch chromatography after SMB chromatography with OR-5, as described in Example 6.

To further exemplify the significant increase in THC free bed volumes provided by performing bulk THC removal with SMB chromatography prior to trace THC removal with batch chromatography, an overlay graph compiling the results of Trials 1-3 of FIGS. 9-11 was created showing the accumulated THC (wt/wt %) as a function of bed volume (L/L) for (i) using OR-1 adsorbent in a batch chromatographic mode to purify a mixture having approximately 2.03 wt % THC (Trial 1), (ii) using OR-1 adsorbent in a batch chromatographic mode to purify a mixture having approximately 0.6 wt % THC (Trial 2), and (iii) using OR-1 adsorbent in a batch chromatographic mode to purify a mixture having approximately 0.35 wt % THC (Trial 3). The results are set forth in FIG. 12. As is apparent from the results set forth in FIG. 12, performing bulk THC removal with SMB chromatography to achieve as low as 0.6 wt % or 0.35 wt % prior to trace THC removal with batch chromatography significantly increases the number of THC free bed volumes, as evidenced by the delayed accumulation of THC.

This example demonstrates that SMB chromatography in combination with batch chromatography can be applied for improved THC breakthrough as compared to batch chromatography alone for a range of THC concentrations. More particular, reducing the SMB chromatography primary raffinate to 0.9 wt % THC and lower (e.g., 0.6 wt % or 0.35 wt %) significantly increases the number of THC free bed volumes, relative to purifying with batch chromatography alone.

Example 7—OR-3 SMB Technology for THC Removal from CBC Feedstock

Figure 13:
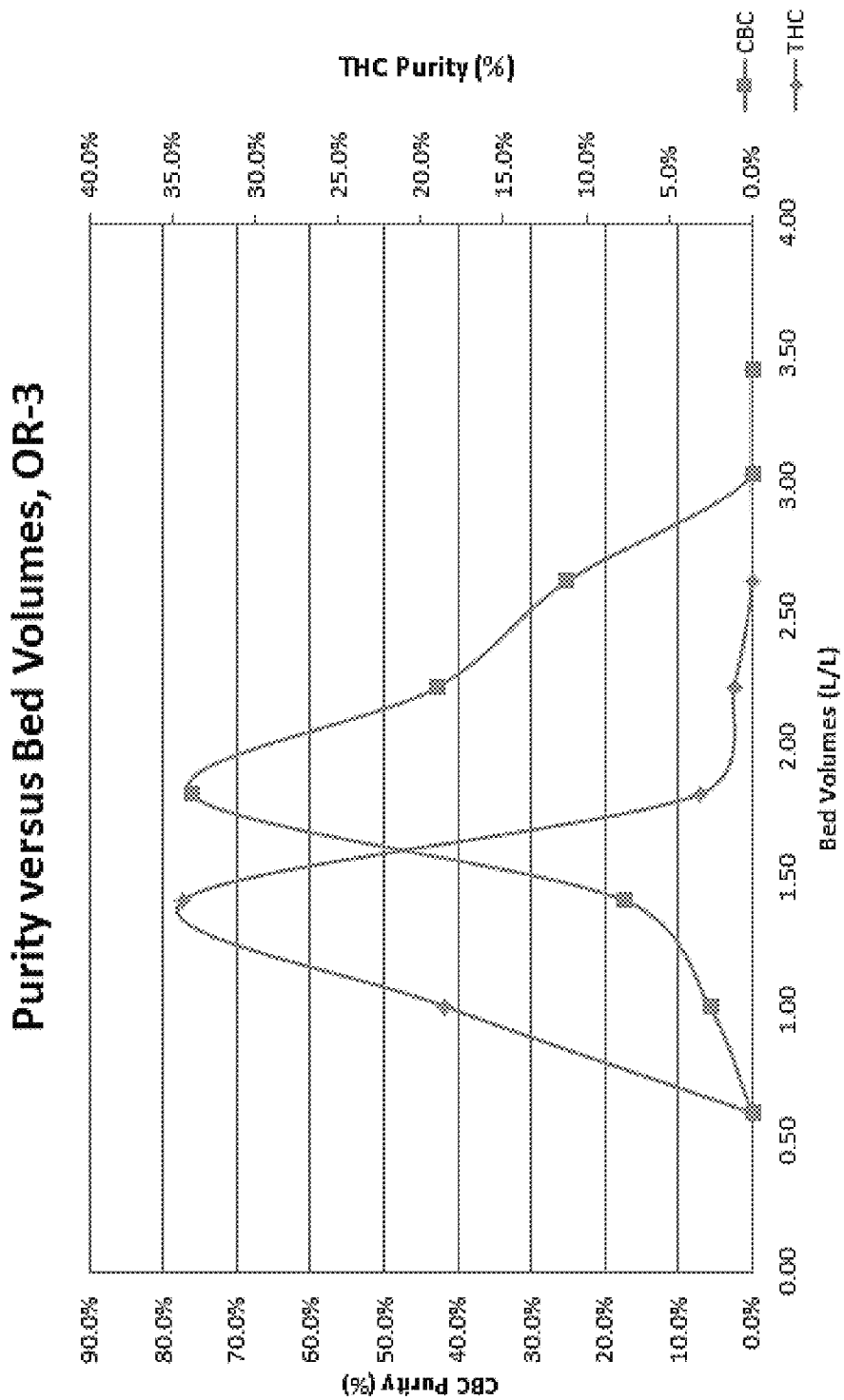
FIG. 13 is a graph showing the normalized peak area count (%) vs. bed volume (L) for THC and CBD processed by a single column OR-3 pulse test, as described in Example 7.

High CBC/THC extract (SMB extract stream), which is decolorized and decarboxylated was used obtained. To the CBC/THC extract was added solvent (90-100 v/v to 10-0 v/v Heptane to IPA). The resulting solution was concentrated to a concentration of 125 mg/mL containing 29.6 wt % CBC and 10.2 wt % THC. The concentrated feed (4.08 mL) was fed into an OR-3 column (22 mm in diameter and 300 mm in length) in a pulsed format. The column effluent was collected in 5 mL fractions. After the concentrated feed was pulsed into the OR-3 column, the mobile phase of a primarily heptane based solvent was fed at a flow rate of 5 mL/min. The resulting fraction compositions were analyzed by HPLC using area count and concentration, and the results for the OR-3 are set forth in FIG. 13. As is apparent from the results set forth in FIG. 13, silica adsorbent OR-3 provides good separation of CBC from THC, as evidenced by the resolution of the peaks in the single column pulse test.

To further demonstrate the ability of OR-3 to separate CBC from THC, SMB technology extract, as described in Example 5, was used as feed to purify CBC by removal of THC using SMB technology with OR-3 as the adsorbent. In the pilot scale run, 114.15 mg of decolorized extract was dissolved for every mL of solvent (97/3 v/v Heptane/IPA, from Pharmco-Aaper). Eight columns, each measuring 4 inches in diameter and 300 inches in length, were connected to the Simulated Moving Bed instrument (from Semba Bioscience—WI, USA). Four pumps (0-300 mL/min) were also connected to the SMB Instrument. The columns were configured to run a 2-3-2-1 scheme. The SMB Step time was set at 1230 seconds and the system was maintained at 25° C. The flow rates for the above-mentioned streams are tabulated in Table 8 and the weight percentages and mass distribution percentages are set forth in Table 9.

TABLE 8

Flow Rates for the Zones in SMB of Example 7

| | Flow rate (mL/min) |
|---|---|
| Desorbent (Zone 1 In) | 300 |
| Feed | 8.4 |
| Extract In (Zone 2 In) | 195.5 |
| Primary Raffinate (Zone 3 Out) | 117.1 |
| Secondary Raffinate (Zone 4 Out) | 86.8 |

TABLE 9

Mass Percent in Each Bulk Stream in SMB of Example 7

| | Concentration (wt %) | |
|---|---|---|
| SMB Input | CBC | THC |
| Feed | 22.65 | 9.76 |

| | Concentration (wt %) | | Mass Distribution (%) | |
|---|---|---|---|---|
| SMB Output | CBC | THC | CBC | THC |
| Extract | 61.24 | 0.11 | 97.03 | 0 |
| Primary Raffinate | 1.45 | 18.97 | 2.69 | 99.77 |
| Secondary Raffinate | 2.54 | 0.73 | 0.28 | 0.23 |

As is apparent from the results set forth in Table 9, the majority of the CBC was isolated in the SMB extract stream, whereas the majority of the THC was found in the SMB primary raffinate stream.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. As used herein, the term "exemplary" indicates an example thereof and does not suggest a best or optimal of the recited item. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of removing THC and/or THCA from a mixture, the mixture including THC and/or THCA and at least one cannabinoid, the method comprising:
   preparing a first feedstock stream from the mixture, the first feedstock stream comprising THC and/or THCA, at least one cannabinoid, and a first solvent;
   passing the first feedstock stream through a first chromatographic resin arranged in a simulated moving bed (SMB) chromatography configuration to provide a primary raffinate stream and an SMB extract stream, the primary raffinate stream having less than 0.9 wt % THC on a solvent free basis and optionally a higher weight percentage of at least one cannabinoid than in the first feedstock stream on a solvent free basis;
   optionally removing at least a portion of the first solvent from the primary raffinate stream to produce a concentrated primary raffinate stream;
   preparing a second feedstock stream, the second feedstock stream comprising the primary raffinate stream or the concentrated primary raffinate stream and a second solvent and the second feedstock stream having less than 0.9 wt % THC on a solvent free basis; and
   passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

2. The method of claim 1, wherein the at least one cannabinoid is cannabidiol (CBD), cannabidiolic acid (CBDA), or a mixture thereof.

3. The method of claim 1, wherein the first chromatographic resin and the second chromatographic resin are each independently selected from:
   (i) an activated carbon adsorbent,
   (ii) a silica adsorbent,
   (iii) a hydrophobic divinylbenzene-based adsorbent,
   (iv) an activated alumina adsorbent,
   (v) a reverse phase carbon-based adsorbent, and
   (vi) a combination thereof.

4. The method of claim 1, wherein the first chromatographic resin is a hydrophobic divinylbenzene-based adsorbent.

5. The method of claim 4, wherein the hydrophobic divinylbenzene-based adsorbent has:
   (i) an average particle diameter of 20 microns to 600 microns,
   (ii) an average surface area of 450 $m^2/g$ to 900 $m^2/g$,
   (iii) an average pore size of 75 Å to 550 Å,
   (iv) an average water content of 35% to 80%,
   (v) an average bulk density of 0.45 g/mL to 0.9 g/mL, or
   (vi) any combination thereof.

6. The method of claim 4, wherein the hydrophobic divinylbenzene-based adsorbent is a polystyrene-divinylbenzene adsorbent.

7. The method of claim 1, wherein the second chromatographic resin is an activated carbon adsorbent.

8. The method of claim 7, wherein the activated carbon adsorbent has:
   (i) an average particle diameter of 40 microns to 1700 microns,
   (ii) an iodine number of 900 mg/g or more, or
   (iii) a combination thereof.

9. The method of claim 1, wherein the second chromatographic resin is disposed in a single column or more than one column in series.

10. The method of claim 1, wherein the second chromatographic resin is arranged in a simulated moving bed (SMB) chromatography configuration.

11. A method of removing THC and/or THCA from a mixture, the mixture including THC and/or THCA and at least one cannabinoid, the method comprising:
    preparing a first feedstock stream from the mixture, the first feedstock stream comprising THC and/or THCA, at least one cannabinoid, and a first solvent;
    passing the first feedstock stream through a first chromatographic resin arranged in a simulated moving bed (SMB) chromatography configuration to provide a primary raffinate stream and an SMB extract stream, the SMB extract stream having a higher weight percentage of THC and/or THCA on a solvent free basis and optionally a higher weight percentage of at least one cannabinoid than in the first feedstock stream on a solvent free basis;
    optionally removing at least a portion of the first solvent from the SMB extract stream to produce a concentrated SMB extract stream;
    preparing a second feedstock stream, the second feedstock stream comprising the SMB extract stream or the concentrated SMB extract stream and a second solvent; and
    passing the second feedstock stream through a second chromatographic resin to provide an eluate stream, the eluate stream having less than 0.3 wt % THC on a solvent free basis and optionally a higher weight percentage of at least one cannabinoid than in the second feedstock stream on a solvent free basis.

12. The method of claim 11, wherein the at least one cannabinoid comprises cannabichromene (CBC).

13. The method of claim 11, wherein the first chromatographic resin and the second chromatographic resin are each independently selected from:
    (i) an activated carbon adsorbent,
    (ii) a silica adsorbent,
    (iii) a hydrophobic divinylbenzene-based adsorbent,
    (iv) an activated alumina adsorbent,
    (v) a reverse phase carbon-based adsorbent, and
    (vi) a combination thereof.

14. The method of claim 11, wherein the first chromatographic resin is a hydrophobic divinylbenzene-based adsorbent.

15. The method of claim 14, wherein the hydrophobic divinylbenzene-based adsorbent has:
    (i) an average particle diameter of 20 microns to 600 microns,
    (ii) an average surface area of 450 $m^2/g$ to 900 $m^2/g$,
    (iii) an average pore size of 75 Å to 550 Å,
    (iv) an average water content of 35% to 80%,
    (v) an average bulk density of 0.45 g/mL to 0.9 g/mL, or
    (vi) any combination thereof.

16. The method of claim 14, wherein the hydrophobic divinylbenzene-based adsorbent is a polystyrene-divinylbenzene adsorbent.

17. The method of claim 11, wherein the second chromatographic resin is a silica adsorbent.

18. The method of claim 17, wherein the silica adsorbent has:
    (i) an average particle diameter of 25 microns to 300 microns,
    (ii) an average surface area of 350 $m^2/g$ to 850 $m^2/g$, (iii) an average pore size of 40 Å to 1000 Å,
(iv) an average bulk density of 0.4 g/mL to 0.8 g/mL,
(v) an average pore volume of 0.7 mL/g to 0.85 mL/g, or
(vi) any combination thereof.

19. The method of claim 11, wherein the second chromatographic resin is disposed in a single column or more than one column arranged in series.

20. The method of claim 11, wherein the second chromatographic resin is arranged in a simulated moving bed (SMB) chromatography configuration.

21. A method of removing THC and/or THCA from a mixture, the mixture including THC and/or THCA and at least one cannabinoid, the method comprising:
    preparing a first feedstock stream from the mixture, the first feedstock stream comprising THC and/or THCA, at least one cannabinoid, and a first solvent;
    passing the first feedstock stream through a first chromatographic resin arranged in a simulated moving bed (SMB) chromatography configuration to provide a primary raffinate stream and an SMB extract stream, wherein passing the first feedstock stream through the first chromatographic resin arranged in a simulated moving bed (SMB) chromatography configuration removes greater than 50 wt % of the THC from the mixture as measured by the mass of THC in the primary raffinate compared to the mass of THC in the mixture;
    optionally removing at least a portion of the first solvent from the primary raffinate stream to produce a concentrated primary raffinate stream;
    preparing a second feedstock stream, the second feedstock stream comprising the primary raffinate stream or the concentrated primary raffinate stream and a second solvent; and
    passing the second feedstock stream through a second chromatographic resin to provide an eluate stream, wherein passing the second feedstock stream through the second chromatographic resin removes up to 50 wt % of the THC from the mixture as measured by the mass of THC in the eluate stream compared to the mass of THC in the mixture.

22. The method of claim 21, wherein the at least one cannabinoid is cannabidiol (CBD), cannabidiolic acid (CBDA), or a mixture thereof.

23. The method of claim 21, wherein the first chromatographic resin and the second chromatographic resin are each independently selected from:
    (i) an activated carbon adsorbent,
    (ii) a silica adsorbent,
    (iii) a hydrophobic divinylbenzene-based adsorbent,
    (iv) an activated alumina adsorbent,
    (v) a reverse phase carbon-based adsorbent, and
    (vi) a combination thereof.

24. The method of claim 21, wherein the first chromatographic resin is a hydrophobic divinylbenzene-based adsorbent.

25. The method of claim 24, wherein the hydrophobic divinylbenzene-based adsorbent has:
    (i) an average particle diameter of 20 microns to 600 microns,
    (ii) an average surface area of 450 $m^2/g$ to 900 $m^2/g$,
    (iii) an average pore size of 75 Å to 550 Å,
    (iv) an average water content of 35% to 80%,
    (v) an average bulk density of 0.45 g/mL to 0.9 g/mL, or
    (vi) any combination thereof.

26. The method of claim 24, wherein the hydrophobic divinylbenzene-based adsorbent is a polystyrene-divinylbenzene adsorbent.

27. The method of claim 21, wherein the second chromatographic resin is an activated carbon adsorbent.

28. The method of claim 27, wherein the activated carbon adsorbent has:
    (i) an average particle diameter of 40 microns to 1700 microns,
    (ii) an iodine number of 900 mg/g or more, or
    (iii) a combination thereof.

29. The method of claim 21, wherein the second chromatographic resin is disposed in a single column or more than one column in series.

30. The method of claim 21, wherein the second chromatographic resin is arranged in a simulated moving bed (SMB) chromatography configuration.

* * * * *